(12) United States Patent
Dharmadhikari et al.

(10) Patent No.: US 9,616,029 B2
(45) Date of Patent: *Apr. 11, 2017

(54) ABUSE DETERRENT IMMEDIATE RELEASE COATED RESERVOIR SOLID DOSAGE FORM

(71) Applicant: SUN PHARMA ADVANCED RESEARCH COMPANY LTD., Mumbai (IN)

(72) Inventors: Nitin Bhalachandra Dharmadhikari, Mumbai (IN); Yashoraj Rupsinh Zala, Mumbai (IN); Dilip Shanghvi, Mumbai (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/667,834

(22) Filed: Mar. 25, 2015

(65) Prior Publication Data

US 2015/0320689 A1    Nov. 12, 2015

(30) Foreign Application Priority Data

Mar. 26, 2014  (IN) .......................... 1041/MUM/2014
Jul. 23, 2014  (IN) .......................... 2378/MUM/2014
Sep. 13, 2014  (IN) .......................... 2917/MUM/2014
Jan. 8, 2015  (IN) ............................. 74/MUM/2015

(51) Int. Cl.
*A61K 9/28*     (2006.01)
*A61K 9/48*     (2006.01)
*A61K 31/137*   (2006.01)
*A61K 31/5517*  (2006.01)
*A61K 9/20*     (2006.01)
*A61K 31/433*   (2006.01)
*A61K 9/50*     (2006.01)

(52) U.S. Cl.
CPC .......... *A61K 9/2846* (2013.01); *A61K 9/2009* (2013.01); *A61K 9/2027* (2013.01); *A61K 9/2081* (2013.01); *A61K 9/4808* (2013.01); *A61K 31/137* (2013.01); *A61K 31/433* (2013.01); *A61K 31/5517* (2013.01); *A61K 9/5026* (2013.01)

(58) Field of Classification Search
CPC .. A61K 9/2846; A61K 9/4808; A61K 31/137; A61K 31/5517; A61K 9/2009; A61K 9/2027; A61K 9/2081; A61K 9/5026; A61K 31/433

See application file for complete search history.

(56) References Cited

U.S. PATENT DOCUMENTS

| | | |
|---|---|---|
| 3,065,143 A | 11/1962 | Christenson et al. |
| 3,260,646 A | 7/1966 | Paulsen et al. |
| 4,070,494 A | 1/1978 | Hoffmeister et al. |
| 4,175,119 A | 11/1979 | Porter |
| 4,221,778 A | 9/1980 | Raghunathan |
| 4,389,393 A | 6/1983 | Schor et al. |
| 4,457,933 A | 7/1984 | Gordon et al. |
| 4,459,278 A | 7/1984 | Porter |
| 4,599,342 A | 7/1986 | LaHann |
| 4,610,870 A | 9/1986 | Jain et al. |
| 4,666,705 A | 5/1987 | DeCrosta et al. |
| 4,800,083 A | 1/1989 | Hom et al. |
| 4,801,461 A | 1/1989 | Hamel |
| 4,915,952 A | 4/1990 | Ayer et al. |
| 4,952,402 A | 8/1990 | Sparks |
| 5,059,600 A | 10/1991 | Gawin et al. |
| 5,073,380 A | 12/1991 | Babu |
| 5,075,114 A | 12/1991 | Roche |
| 5,084,278 A | 1/1992 | Mehta |
| 5,098,715 A | 3/1992 | McCabe |
| 5,114,942 A | 5/1992 | Gawin et al. |
| 5,273,758 A | 12/1993 | Royce |
| 5,284,662 A | 2/1994 | Koparkar et al. |
| 5,330,766 A | 7/1994 | Morelia et al. |
| 5,405,617 A | 4/1995 | Gowan, Jr. |
| 5,431,916 A | 7/1995 | White |
| 5,484,606 A | 1/1996 | Dhabhar |
| 5,508,042 A | 4/1996 | Oshlack et al. |
| 5,558,879 A | 9/1996 | Chen |
| 5,654,005 A | 8/1997 | Chen |
| 5,741,524 A | 4/1998 | Staniforth et al. |
| 5,807,579 A | 9/1998 | Vilkov |
| 5,840,337 A | 11/1998 | Cody |
| 5,858,409 A | 1/1999 | Karetny |
| 5,895,663 A | 4/1999 | Irwin et al. |
| 5,916,590 A | 6/1999 | Cody et al. |
| 5,919,481 A | 7/1999 | Cody et al. |
| 5,955,107 A | 9/1999 | Augello |
| 5,968,551 A | 10/1999 | Oshlack et al. |
| 5,997,905 A | 12/1999 | McTeigue |
| 6,024,980 A | 2/2000 | Hoy |
| 6,027,746 A | 2/2000 | Lech |
| 6,136,864 A | 10/2000 | Nichols et al. |
| 6,153,621 A | 11/2000 | Hamann |
| 6,197,314 B1 | 3/2001 | Elnig |

(Continued)

*Primary Examiner* — Sean Basquill

(74) *Attorney, Agent, or Firm* — Sughrue Mion, PLLC

(57) ABSTRACT

An abuse deterrent immediate release coated reservoir solid dosage form that releases the drug at a desired rate for quick onset of action when a single unit or prescribed units of the dosage form are orally administered but exhibits a reduced rate of release when more than the prescribed number of units, are administered.

3 Claims, 9 Drawing Sheets

(56) References Cited

U.S. PATENT DOCUMENTS

| | | |
|---|---|---|
| 6,210,710 B1 | 4/2001 | Skinner |
| 6,217,903 B1 | 4/2001 | Skinner |
| 6,228,863 B1 | 5/2001 | Palermo et al. |
| 6,248,363 B1 | 6/2001 | Patel et al. |
| 6,277,409 B1 | 8/2001 | Luber |
| 6,294,192 B1 | 9/2001 | Patel |
| 6,309,663 B1 | 10/2001 | Patel et al. |
| 6,309,668 B1 | 10/2001 | Bastin et al. |
| 6,340,471 B1 | 1/2002 | Kershman et al. |
| 6,352,721 B1 | 3/2002 | Faour |
| 6,358,525 B1 | 3/2002 | Guo |
| 6,359,011 B1 | 3/2002 | Bess et al. |
| 6,375,957 B1 | 4/2002 | Kaiko et al. |
| 6,383,471 B1 | 5/2002 | Chen et al. |
| 6,432,442 B1 | 8/2002 | Buehler |
| 6,471,991 B2 | 10/2002 | Robinson |
| 6,488,963 B1 | 12/2002 | McGinity et al. |
| 6,491,949 B2 | 12/2002 | Faour et al. |
| 6,495,529 B1 | 12/2002 | Booth |
| 6,500,459 B1 | 12/2002 | Chhabra |
| 6,514,531 B1 | 2/2003 | Alaux et al. |
| 6,524,618 B1 | 2/2003 | Kumar et al. |
| 6,541,025 B1 | 4/2003 | Kershman et al. |
| 6,551,617 B1 | 4/2003 | Corbo |
| 6,559,159 B2 | 5/2003 | Carroll et al. |
| 6,572,885 B2 | 6/2003 | Oshlack et al. |
| 6,589,556 B2 | 7/2003 | Cherukuri |
| 6,592,901 B2 | 7/2003 | Durig et al. |
| 6,593,367 B1 | 7/2003 | Dewey et al. |
| 6,607,748 B1 | 8/2003 | Lenaerts |
| 6,613,357 B2 | 9/2003 | Faour |
| 6,753,009 B2 | 6/2004 | Luber et al. |
| 6,800,668 B1 | 10/2004 | Odidi |
| 6,814,979 B2 | 11/2004 | Rudnic |
| 6,923,988 B2 | 8/2005 | Patel et al. |
| RE39,069 E | 4/2006 | Faour |
| 7,090,867 B2 | 8/2006 | Odidi et al. |
| 7,101,572 B2 | 9/2006 | Santos |
| 7,141,250 B2 | 11/2006 | Oshlack et al. |
| 7,144,587 B2 | 12/2006 | Oshlack et al. |
| 7,157,100 B2 | 1/2007 | Doshi et al. |
| 7,157,103 B2 | 1/2007 | Sackler |
| 7,192,966 B2 | 3/2007 | Mayo-Alvarez |
| 7,201,920 B2 | 4/2007 | Kumar et al. |
| 7,332,182 B2 | 2/2008 | Sackler |
| 7,374,779 B2 | 5/2008 | Chen et al. |
| 7,384,653 B2 | 6/2008 | Wright et al. |
| 7,476,402 B2 | 1/2009 | Kumar et al. |
| 7,510,726 B2 | 3/2009 | Kumar et al. |
| 7,524,515 B2 | 4/2009 | Roberts |
| 7,611,728 B2 | 11/2009 | Kidane |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholamaus et al. |
| 7,879,352 B2 | 2/2011 | Solomon et al. |
| 7,897,179 B2 | 3/2011 | Mulye |
| 7,906,143 B1 | 3/2011 | Odidi |
| 8,114,383 B2 | 2/2012 | Bartholomaus et al. |
| 8,273,798 B2 | 9/2012 | Bausch et al. |
| 8,389,007 B2 | 3/2013 | Wright et al. |
| 8,420,700 B1 | 4/2013 | Bausch et al. |
| 9,101,636 B2 | 8/2015 | Brzeczko et al. |
| 9,320,796 B2 | 4/2016 | Brzeczko et al. |
| 2002/0022057 A1 | 2/2002 | Battey |
| 2002/0119196 A1 | 8/2002 | Parikh |
| 2003/0004177 A1 | 1/2003 | Kao et al. |
| 2003/0021841 A1 | 1/2003 | Matharu |
| 2003/0039691 A1 | 2/2003 | Waterman |
| 2003/0049272 A1 | 3/2003 | Joshi et al. |
| 2003/0049320 A1 | 3/2003 | Bhagwatwar |
| 2003/0050620 A1 | 3/2003 | Odidi |
| 2003/0059471 A1 | 3/2003 | Compton |
| 2003/0064099 A1 | 4/2003 | Oshlack et al. |
| 2003/0064122 A1 | 4/2003 | Goldberg et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler et al. |
| 2003/0096791 A1 | 5/2003 | Gupte |
| 2003/0099711 A1 | 5/2003 | Meadows |
| 2003/0124061 A1 | 7/2003 | Roberts et al. |
| 2003/0124185 A1 | 7/2003 | Oshlack et al. |
| 2003/0125347 A1 | 7/2003 | Anderson et al. |
| 2003/0170181 A1 | 9/2003 | Midha |
| 2003/0180362 A1 | 9/2003 | Park |
| 2003/0232081 A1 | 12/2003 | Doshi et al. |
| 2004/0081695 A1 | 4/2004 | Sowden |
| 2004/0109889 A1 | 6/2004 | Bunick |
| 2004/0131552 A1 | 7/2004 | Boehm |
| 2004/0151791 A1 | 8/2004 | Mayo-Alvarez et al. |
| 2004/0185097 A1 | 9/2004 | Kannan |
| 2004/0228802 A1 | 11/2004 | Chang et al. |
| 2004/0265372 A1 | 12/2004 | Wynn et al. |
| 2005/0013857 A1 | 1/2005 | Fu |
| 2005/0020613 A1 | 1/2005 | Boehm et al. |
| 2005/0063909 A1 | 3/2005 | Wright et al. |
| 2005/0106249 A1 | 5/2005 | Hwang et al. |
| 2005/0112067 A1 | 5/2005 | Kumar et al. |
| 2005/0163851 A1 | 7/2005 | Feleder |
| 2006/0003007 A1 | 1/2006 | Odidi et al. |
| 2006/0008527 A1 | 1/2006 | Lagoviyer |
| 2006/0013876 A1 | 1/2006 | Lohray |
| 2006/0018837 A1 | 1/2006 | Preston et al. |
| 2006/0029661 A1 | 2/2006 | Radhakrishnan |
| 2006/0057210 A1 | 3/2006 | Oshlack et al. |
| 2006/0093631 A1 | 5/2006 | Buehler |
| 2006/0105038 A1 | 5/2006 | Lai et al. |
| 2006/0110327 A1 | 5/2006 | Emigh et al. |
| 2006/0177380 A1 | 8/2006 | Emigh et al. |
| 2007/0042044 A1 | 2/2007 | Fischer et al. |
| 2007/0065510 A1 | 3/2007 | Odidi et al. |
| 2007/0134493 A1 | 6/2007 | Meghpara |
| 2007/0215511 A1 | 9/2007 | Mehta |
| 2007/0292510 A1 | 12/2007 | Huang |
| 2008/0014228 A1 | 1/2008 | Darmuzey |
| 2008/0069878 A1 | 3/2008 | Venkatesh et al. |
| 2008/0095843 A1 | 4/2008 | Nutalapati |
| 2008/0152595 A1 | 6/2008 | Emigh et al. |
| 2008/0260837 A1 | 10/2008 | Namburi |
| 2008/0287456 A1 | 11/2008 | Roberts |
| 2008/0305166 A1 | 12/2008 | Durig |
| 2008/0312168 A1 | 12/2008 | Pilgaonkar et al. |
| 2008/0312264 A1 | 12/2008 | Arkenau-Maric et al. |
| 2008/0317854 A1 | 12/2008 | Arkenau et al. |
| 2009/0004281 A1 | 1/2009 | Nghiem |
| 2009/0005408 A1 | 1/2009 | Arkena-Maric et al. |
| 2009/0081290 A1 | 3/2009 | McKenna et al. |
| 2009/0081291 A1 | 3/2009 | Gin |
| 2009/0098200 A1 | 4/2009 | Krayz et al. |
| 2009/0142378 A1 | 6/2009 | Frisbee |
| 2009/0175937 A1 | 7/2009 | Rahmouni et al. |
| 2009/0202634 A1 | 8/2009 | Jans et al. |
| 2009/0208576 A1 | 8/2009 | Gandhi |
| 2009/0232887 A1 | 9/2009 | Odidi et al. |
| 2009/0311327 A1 | 12/2009 | Roberts |
| 2009/0317355 A1 | 12/2009 | Roth et al. |
| 2010/0010101 A1 | 1/2010 | Cherukuri |
| 2010/0015223 A1 | 1/2010 | Cailly-Dufestel et al. |
| 2010/0015224 A1 | 1/2010 | Singh |
| 2010/0092555 A1 | 4/2010 | Wynn et al. |
| 2010/0151028 A1 | 6/2010 | Ashworth et al. |
| 2010/0249045 A1 | 9/2010 | Babul |
| 2010/0255063 A1 | 10/2010 | Andersen |
| 2010/0260842 A1 | 10/2010 | Nair |
| 2010/0266666 A1 | 10/2010 | Andersen |
| 2010/0291183 A1* | 11/2010 | Farrell .................. A61K 9/284 424/443 |
| 2010/0297031 A1 | 11/2010 | Ubeda |
| 2010/0330150 A1 | 12/2010 | Venkatesh |
| 2011/0020440 A1 | 1/2011 | Modi |
| 2011/0028456 A1 | 2/2011 | Lulla |
| 2011/0077238 A1 | 3/2011 | Leech |

(56) References Cited

U.S. PATENT DOCUMENTS

| | | |
|---|---|---|
| 2011/0129530 A1* | 6/2011 | Venkatesh ............ A61K 9/0056 |
| | | 424/470 |
| 2011/0142942 A1* | 6/2011 | Schobel ................ A61K 9/006 |
| | | 424/489 |
| 2011/0207761 A1 | 8/2011 | Losev et al. |
| 2013/0022646 A1 | 1/2013 | Rudnic et al. |
| 2013/0065885 A1 | 3/2013 | Roberts et al. |
| 2015/0017240 A1 | 1/2015 | Shah et al. |
| 2015/0118302 A1 | 4/2015 | Haswani et al. |
| 2015/0272902 A1* | 10/2015 | Dharmadhikari .... A61K 31/137 |
| | | 424/487 |
| 2016/0199388 A1 | 7/2016 | Brzeczko et al. |

\* cited by examiner

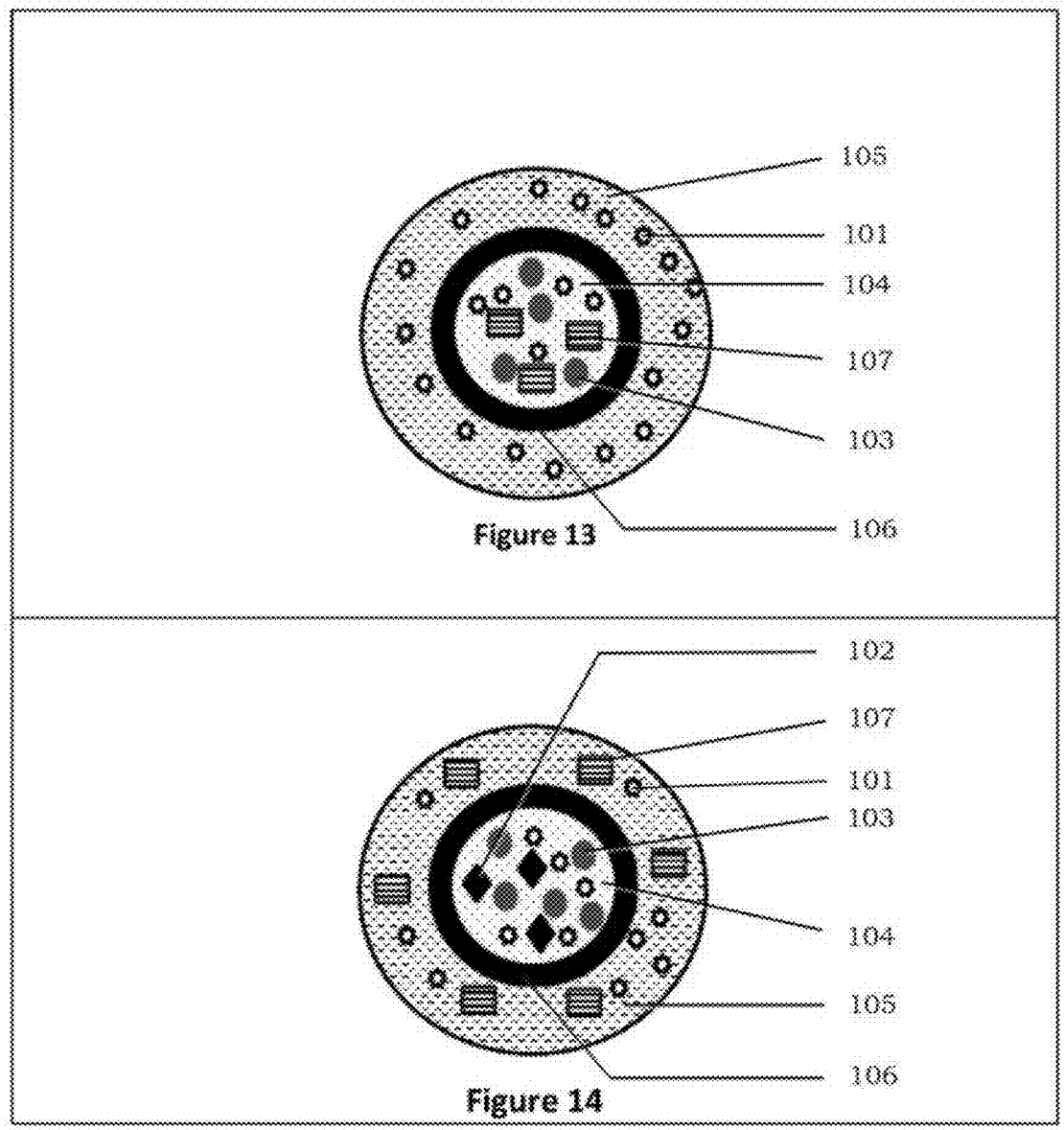

ABUSE DETERRENT IMMEDIATE RELEASE COATED RESERVOIR SOLID DOSAGE FORM

BACKGROUND OF THE INVENTION

Field

The present invention relates to abuse deterrent immediate release coated reservoir solid dosage form that releases the drug at a desired rate for quick onset of action when a single unit or prescribed units of the dosage form are orally administered but exhibits a reduced rate of release when more than the prescribed number of units, are administered. When an abuser, with the objective of achieving a high blood concentration of the drug uses multiple units of the dosage forms through multiple modes of abuse such as extraction or ingestion, he encounters resistance of the dosage form to release high amounts of the drug and provide high blood concentration.

Abuse of prescription drugs is considered an epidemic. Abuse of the prescription behavior may be for satisfying the craving for an addictive drug. It may be for improvement of performance such as use of steroids and stimulants. Prescription drugs may also be abused for abetting suicides by taking multiple pills.

An abuser of prescription drugs seeking to satisfy the craving for an addictive drug such as opioids, seeks a potent and rapid "high" i.e. euphoria and this is obtained by achieving a high blood concentration (high "$C_{max}$") in a short time ($T_{max}$) (Katz et al (The American Journal of Drug and Alcohol Abuse, 37:205-257, 2011, Abreu, M. E., G. E. Bigelow, L. Fleisher, S. L. Walsh, 2001, Effect of Intravenous Injection Speed on Responses to Cocaine and Hydromorphone in Humans, *Psychopharmacology*, 154:76-84; de Wit, H., B. Bodker, J. Ambre, 1992, Rate of Increase of Plasma Drug Level Influences Subjective Responses in Humans, *Psychopharmacology*, 107:352-358; and de Wit, H., S. Didish, J. Ambre, 1993, Subjective and Behavioral Effects of Diazepam Depend on Its Rate of Onset, *Psychopharmacology*, 112: 324-330). Extended release dosage forms provide peak plasma concentration at a longer time ($T_{max}$) but because they are given at a lower frequency for example once-a-day they contain a higher amount of drug than immediate release or rapid release dosage forms. Therefore, they are attractive to the abuser when the abuser can tamper with them to destroy the controlled release properties. Thus, one-way to deter misuse is to provide the medication in an extended release form together with design features such as tamper resistance that prevent the abuser from defeating the controlled release properties or extracting the opioid from the dosage form in aqueous or organic liquids. In April 2013, USFDA refused to approve generic versions of Oxycontin extended release formulations that were not tamper-resistant and thus susceptible to abuse. Therefore it is essential to have design features that prevent the abuser from taking a prescription dosage form and tampering it to produce a form suitable for achieving a high $C_{max}$ in a short time ($T_{max}$) through oral administration or administration via fast onset routes such as parenteral or nasal. Commonly the extended release dosage form is indicated for chronic therapy, for example, opioid extended release formulations are indicated for pain severe enough to require daily around-the-clock treatment. Technology for such tamper resistant dosage forms has been available for more than a decade and has been used in recently commercialized opioid products such as Oxcontin® ER Tablets (containing oxycodone hydrochloride as the active ingredient). Examples of such abuse deterrent dosage forms are described in U.S. Pat. Nos. 6,488,963, 7,776,314, 8,114,383, 8,309,060, 8,337,888, 8,075,872, 8,114,384, 8,192,722, 8,420,056, 8,507,001 and 8,298,581.

However, rapid release opioids are also required and are prescribed by physicians when a quick onset of action is needed. For example, Oxcontin® ER Tablets are available in strengths of 10, 15, 20, 30, 40, 60 and 80 mg of oxycodone base, whereas immediate or rapid release Oxycodone Tablets are available in strengths of 5, 7.5, 10, 15, 20 and 30 mg of oxycodone. In view of the liking for a high $C_{max}$ and in view of development of tolerance, chronic abusers graduate to higher and higher dosages of the opioid. Therefore chronic abuser generally requires multiple doses of an immediate or rapid release dosage form. Therefore, dosage forms that release a drug susceptible to abuse rapidly may be subject to abuse by administration of multiple pills.

In addition to opioids, multiple dosage forms of antidepressants, antipsychotic and other CNS drugs are also widely abused in suicidal attempts. Overdose refers to ingestion of a dose greater than a usual dose. "Usual dose' as used herein means a dose approved by a drug regulatory authority such as Food & Drug Administration or prescribed by a physician for treatment or prevention of a diseases condition or relief of symptoms thereof. The high plasma levels of a drug candidate resulting from the overdose, causes adverse effects often leading to medical emergency and inconvenience to his or her family and the medical profession involved. Death is often a consequence of serious overdosing. A person's tolerance to overdose varies with age, state of health, how the substance was consumed and other factors. Death may follow immediately or more slowly if organs are permanently damaged.

A patient may ingest an overdose accidentally or through intentional misuse. In case of accidental overdose, a person takes a wrong drug or combination of drugs, in the wrong amount or at the wrong time inadvertently. On the other hand, in case of intentional misuse, a person takes an overdose to get 'high' or to inflict self-harm. The latter may be a cry for help or a suicide attempt.

Use of medication is increasing world-wide. The United States Food and Drug Administration (USFDA) has approved more than 10000. The reasons may be the introduction of vast number of agents by the advanced pharmaceutical industry in addition to the wide spectrum of diseases that increased demands for intensifying therapeutic challenges. Most commonly, the patient benefits from pharmacotherapeutic interventions; however, adverse events, ranging from minor side effects to death, may occur. Any deviation from the intended beneficial effect of a medication results in a drug related problem (DRP). (Al-Arifi et al., *Saudi Pharmaceutical Journal, January* 2014, 22(1), 17-25).

It has been estimated that DRPs account for 17 million emergency department (ED) visits and 8.7 million hospital admissions annually in the United States. (Johnson et al., *Archives of Internal Medicine, October* 1995, 155(18), 1949-56) Between 1995 and 2000, a probability model estimated that costs associated with morbidity and mortality secondary to DRPs have more than doubled from US$76.6 billion to more than US$177.4 billion. (Ernst et al., *Journal of American Pharmacists Association,* 2001 March-April, 41(2), 192-9). In United States of America, estimates on drug-related visits to hospital emergency departments (ED) are obtained from the Drug Abuse Warning Network (DAWN), which is a public health surveillance system managed by the Substance Abuse and Mental Health Services Administration (SAMHSA), U.S. Department of Health and Human Services (HHS). The DAWN database as updated till 2011 and it reports more than 500 different medications being reported to be consumed accidentally leading the user to make emergency visits. Out of these different medications, the majority of the drugs being overdosed causing emergency situations are mainly, antidepressants, analgesics, hypnotics and sedatives (http://www.samhsa.gov/data/).

One or more DRPs may develop in a given patient after the initial drug therapy. Although many DRPs can be resolved without a major impact on patient's health, some of them can be associated with significant morbidity and mortality. (Classen et al., *Journal of American Medical Association, January* 1997, 277 (4), 301-6). Hepler et al defined DRP as an event or circumstance involving drug treatment that actually or potentially interferes with the patients experiencing an optimum outcome of medical care. They also classified DRPs into eight general categories, which include untreated indication, treatment without indication, improper drug selection, too little drug, too much drug, noncompliance, adverse drug reaction (ADR), and drug interaction (Hepler et al., *American Journal of Hospital Pharmacy,* 1990 March, 47(3), 533-43).

The most common class of drugs reported in literature that cause drug related problems due to intention or unintentional overdose are tricyclic antidepressants (TCS), benzodiazepines, analgesics like paracetamol, aspirin and opioids.

Kerr et al. reviewed the overdose because of tricyclic antidepressants. Overdoses of tricyclic antidepressant are among the commonest causes of drug poisoning seen in accident and emergency department. Complications of tricyclic antidepressant overdose reported were sinus tachycardia, ECG changes, Heart block, Vasodilatation, Hypotension, Cardiogenic shock and Ventricular fibrillation. CNS related complications include Drowsiness, Coma, Convulsions, Pyramidal signs, Rigidity, Delirium, Respiratory depression, Ophthalmoplegia. Different anticholinergic effects observed were Dry mouth Blurred vision, dilated pupils, Urinary retention, absent bowel sounds, Pyrexia, Myoclonic twitching. (Kerr et al., *Emergency Medicine Journal,* 2001, 18, 236-241).

As reported, 20% of deaths were associated with accidental deaths due to overdose whereas 80% were associated with intentional deaths, suggesting that most deaths from antidepressant drugs are due to suicide. Tricyclic antidepressants are associated with a higher number of accidental and intentional deaths, and significantly more accidental (P50.0001) and intentional (P50.001) deaths were observed with the tricyclics than would be expected when standardized for the number of prescriptions. The SSRIs were associated with significantly fewer accidental (P50.0001) and intentional (P50.0001) deaths than would be expected when standardized for the number of prescriptions. For the other antidepressant drugs there was no significant difference (Survjit cheeta et al., *British journal of Psychiatry,* 2004, 184:41-47). Therefore SSRI (selective serotonin reuptake inhibitors) are considered to be less toxic than in overdose than TCA (tricyclic antidepressants). Venlafaxine a SSRI was studied. (Whyte et al., *Quarterly journal of medicine,* 2003, 96, 369-374)

Benzodiazepines are among the most frequently prescribed drugs worldwide. This popularity is based not only on their efficacy but also on their remarkable safety. Pure benzodiazepine overdoses usually induce a mild to moderate central nervous system depression; deep coma requiring assisted ventilation is rare, and should prompt a search for other toxic substances. The severity of the CNS depression is influenced by the dose, the age of the patient and his or her clinical status prior to the ingestion, and the congestion of other CNS depressants. In severe overdoses, benzodiazepines can occasionally induce cardiovascular and pulmonary toxicity, but deaths resulting from pure benzodiazepine overdoses are rare. (Gaudreault P. et al., *Drug Safety,* 1991 July-August, 6(4), 247-65).

It has been reported that between 1993 and 2004, 2,196 poisoning deaths occurred involving paracetamol. Overdose is one of the most frequent indications for patients to be admitted to the medical wards. In the recent past, three changes have occurred which might influence self-poisoning. First, a change in available paracetamol packs size. Secondly, the introduction of new antidepressant drugs some of which, in particular the SSRI group, are perceived as being less toxic in overdose, has resulted in a more than two-fold increase in prescriptions. Thirdly an in increasing use of drugs of abuse, specifically opiates, which is itself associated with an increase in self-harm and suicide. (Bateman et al., *Quarterly Journal of Medicine,* 2003, 96, 125-132).

According to Bohmert et. al, there was increase in rate of unintentional overdose in USA by 124% largely because of the prescription opioids. Higher prescribed doses increase the risk of drug overdose among individuals treated with opioids for chronic non-cancer pain (Bohmert et al., *The journal of the American medical association,* 6 Apr. 2011, vol 305, No. 13).

It is estimated that 52% deaths were caused due overdoses of anticoagulants, insulin and oral hypoglycemic, cardiac glycosides or thyroxine out of which 50% were accidental (D Gunnell et al., *Emergency Medicine Journal,* 2004,21, 35-38).

Brune et all report that aspirin and paracetamol are lethal when taken at overdose. They are best-selling OTC drugs and can pose a significant risk to the consumer who is unaware of the toxicity of these drugs (Brune et al., *Current Rheumatology Reports February,* 2009, Volume 11, Issue 1, 36-40).

For reasons discussed hereinabove, particularly preventing intentional abuse for addiction or suicidal attempt or unintentional/accidental overdosing. there is a need for an abuse deterrent solid dosage form that allows the release of the drug at a desirable rate when a single or prescribed number of units of the dosage form are orally administered but exhibits a reduced rate of release when more than single unit or prescribed number of units, are simultaneously orally administered. The present inventors have discovered coated reservoir solid dosage forms that can resolve at least one of the modes of abuse of immediate release solid dosage form such as a. intentional abuse of overdosing or multiple unit administration by an addict or by a subject having suicidal intention, b. intentional abuse of extraction from multiple unit administration by an addict or by a subject having suicidal intention c. unintentional or accidental overdosing, d. concomitant alcohol consumption and resultant drug-alcohol interaction e. intentional abuse by nasal, parenteral, rectal or oral route f. separating two phases by physical means with an intention to abuse Particular embodiments have been discovered that simultaneously resolve two or three or more of the above modes of abuse. Further embodiments of coated reservoir solid dosage forms have been discovered that are resistant to physical means for separating the two phases with an intention to abuse. The physical means may be crushing the dosage form followed by size separation

SUMMARY OF THE INVENTION

The abuse deterrent immediate release coated reservoir solid dosage form of the present invention comprises a drug susceptible to abuse and a release inhibiting agent such that when more than the prescribed number of units of the dosage form are orally administered, the release is inhibited as compared to the release when a single unit of the dosage form is orally administered. The term 'release inhibiting agent' as used herein refers to a substance or a combination thereof, that functions to inhibit the release of the drug susceptible to abuse in gastric fluids only when more than the prescribed number of units of the dosage form are orally administered. In preferred embodiment, the release inhibiting agent is a combination of one or more reverse enteric polymers and an antacid. The release inhibiting agent either fails to have a significant effect of inhibiting the release when a single unit of the dosage form is orally administered or has no effect. In this way the dosage form of the present invention is useful to deter the abuse of drugs by drug addicts or by individuals seeking to commit suicide. In certain embodiments, where the prescribed number of units of the immediate release of the solid dosage form of the present invention is two, then the composition of the release inhibiting agent used is such that the two prescribed number of units provide the release of the drug which is equivalent to the release obtained from the conventional, immediate release solid dosage form. But, when three or more number of units is tested, the release is inhibited as compared to the equivalent number of units of the conventional immediate release solid dosage form. It is observed that as the number of units of the immediate release solid dosage form of the present invention increases, release rate decreases. This will provide deterrence particularly, against misuse, intentional such as suicidal (overdose) or unintentional, or abuse by an abuser or addict.

The present invention provides an abuse deterrent immediate release coated reservoir solid dosage form that deters the abuse of the drug by multiple pill oral administration as well as abuse by other routes of administration such as nasal, parenteral and rectal.

The present inventors have discovered that certain preferred embodiments of the present invention can provide very high resistance to multiple pill abuse. Particularly they have discovered the preferred mode of incorporating the antacid such as an alkalizer. When a part of the antacid is in the same phase as the reverse enteric polymer i.e in admixture with each other, the combination forms a highly effective release inhibiting agent. Also particularly the present inventors have discovered release inhibiting combination of an antacid and a reverse enteric polymer that is soluble in acidic solutions but insoluble above second higher pH value is surprisingly advantageous as compared to the reverse enteric polymer that is soluble in acidic solutions but which swells or gels above a second higher pH value. When multiple pills are taken by human subjects, the dosage form of the present invention significantly suppresses the in-vivo release and the peak plasma levels of the drug that could arise from the ingestion of multiple pills are significantly suppressed.

The present inventors have further discovered useful abuse deterrent immediate release coated reservoir solid dosage forms capable of deterring multiple modes of abuse including:

a. intentional abuse of overdosing or multiple unit administration by an addict or by a subject having suicidal intention, b. intentional abuse of extraction from multiple unit administration by an addict or by a subject having suicidal intention c. unintentional or accidental overdosing, d. concomitant alcohol consumption and resultant drug-alcohol interaction e. intentional abuse by nasal, parenteral, rectal or oral route f. separating two phases by physical means with an intention to abuse Particular embodiments have been discovered that simultaneously resolve two or three or all four of the above modes of abuse. Further embodiments of coated reservoir solid dosage forms have been discovered that are resistant to physical means for separating the two phases with an intention to abuse. The physical means may be crushing the dosage form followed by size separation.

BRIEF DESCRIPTION OF THE DRAWINGS

FIG. 13 depicts an Abuse Deterrent Immediate Release Solid dosage form of Coated Reservoir System type XIII having a core containing drug, part of the antacid such as alkalizer and second polymer which is an alcohol dose-dumping resistance polymer, the core is coated with reverse enteric polymer, the coated core forming an intragranular phase and a remaining part of the antacid such as alkalizer forming an extragranular phase.

FIG. 14 depicts an Abuse Deterrent Immediate Release Solid dosage form of Coated Reservoir System type XIV having a core containing drug, part of the antacid such as alkalizer and part of the reverse enteric polymer, the core is coated with part of the reverse enteric polymer, the coated core forming the intragranular phase and a part of the antacid such as alkalizer and second polymer which is an alcohol dose-dumping resistance polymer, forming an extragranular phase.

Although not shown in FIGS. 1 to 17, additional properties in the above exemplary Types may be imparted, and particularly, for example where required, embodiments of the solid dosage form of the present invention can be tamper or crush resistant or on crushing and other physical means, the two phases cannot be separated.

Figure 18:
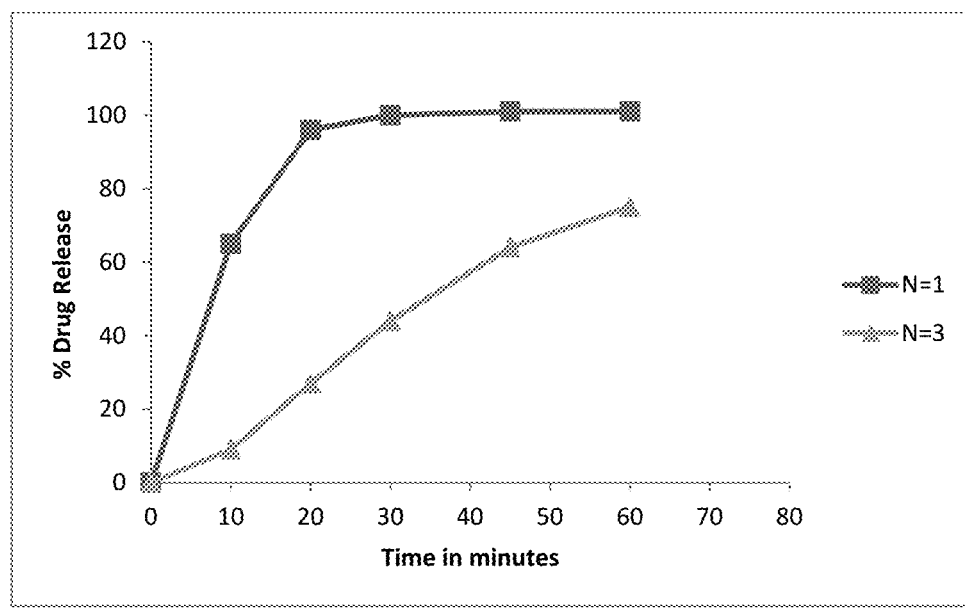

FIG. 18 is the graph of % release of the drug Vs time in minutes for the oral dosage form of Example 1, when N units of the dosage form are placed together in the dissolution bath to check the dissolution release of the drug.

Figure 19:
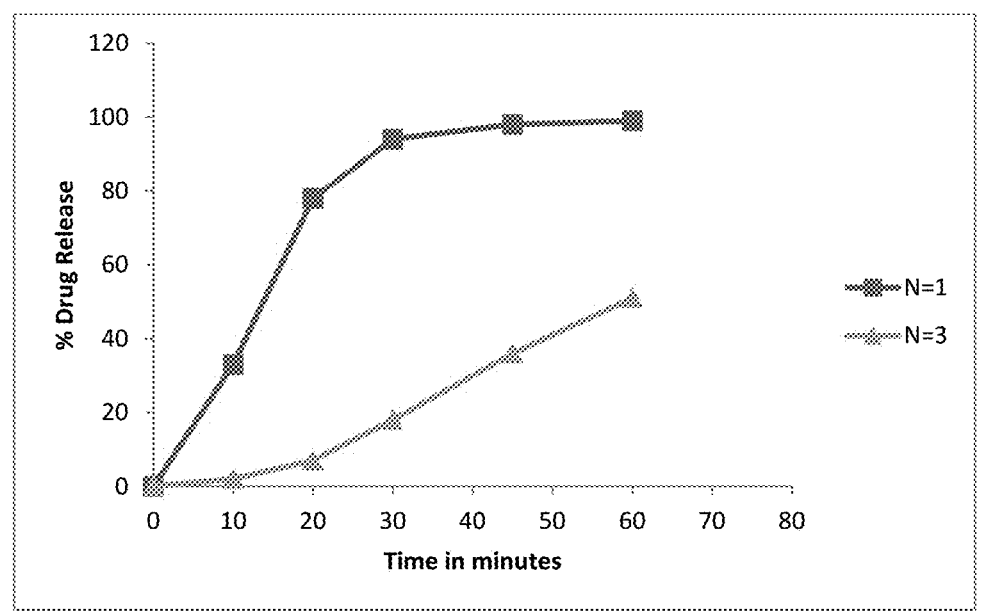

FIG. 19 is the graph of % release of the drug Vs time in minutes for the oral dosage form of Example 2, when N units of the dosage form are placed together in the dissolution bath to check the dissolution release of the drug.

Figure 20:
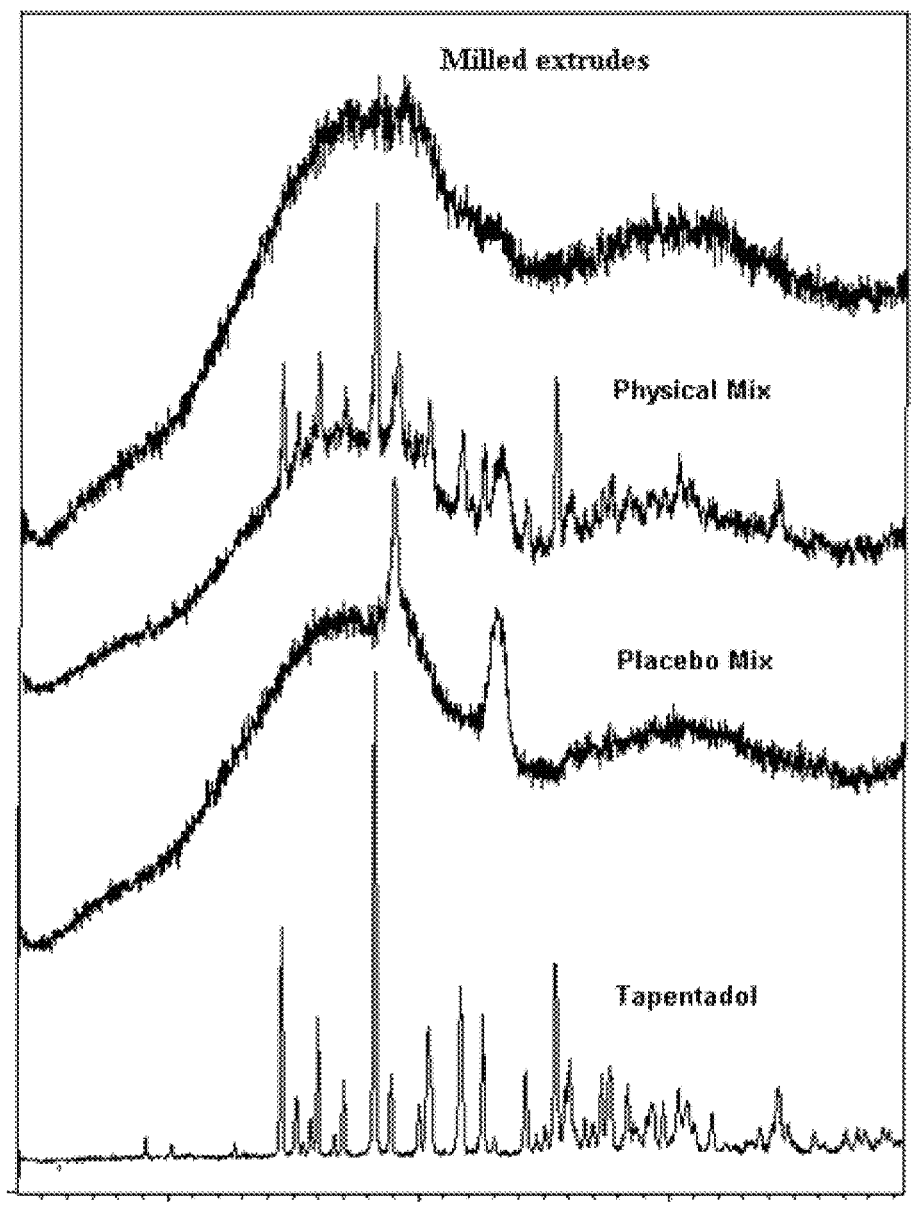

FIG. 20 provides a X-ray diffraction pattern of (i) model drug (Tapentadol), (ii) placebo mixture of reverse enteric polymer and alcohol dose dumping resistance polymer, (iii) physical mixture of drug, reverse enteric polymer and alcohol dose dumping resistance polymer and (iv) milled extrudates of drug with reverse enteric polymer and alcohol dose dumping resistance polymer.

Item 101 represents antacid.
Item 102—represents reverse enteric polymer.
Item 103 represents drug.
Item 104 represents intragranular phase.
Item 105 represents extragranular phase
Item 106 represents coating containing reverse enteric polymer.
Item 107 represents alcohol dose dumping resistance polymer or polymer providing tamper resistance.
Item 108 represents coating containing reverse enteric polymer and water insoluble polymer.

DEFINITIONS

The term 'abuse' as used herein means the ingestion of the drugs by individuals with the intention of achieving a feel of high. The term 'abuse' also covers the over-ingestion of the drug intentionally or unintentionally. In case of intentional abuse it may be an attempt to suicide or in case of unintentional, it may be accidental consumption of more number of units of the drugs than the prescribed.

The phrase 'release inhibiting agent' used herein means agent that inhibits the release of the drug. According to the present invention, the release inhibiting agent is a combination of one or more polymers and an antacid wherein at least one polymer is a reverse enteric polymer.

The term, "reverse enteric polymer" as used herein refers to a polymer that is soluble in acidic solutions but is insoluble or alternatively swells or gels above a second higher pH value. Whether a polymer is insoluble above the second pH value is determined as follows:

500 mg of the reverse enteric polymer is dispersed in 100 ml of 0.05 N HCL and its pH adjusted to the second pH value by adding an alkali. Percent transmission of the dispersion is measured at 260 nm. The reverse enteric polymer is defined as 'insoluble' at and above the second specific pH value, if the percent transmission obtained at the second pH value is below 70%.

The term 'antacid' as used herein means any agent that suppresses the gastric acid environment. The antacid may work by physicochemical mechanisms that result in inhibition of in-vitro release as well as in-vivo release. For example, an alkalizer can increase the pH by neutralization of acid.

The term "granular" as used herein means an agglomerate of multiple particles bound together physically and encompassing granules, extrudates, pellets, pills, and the like.

The term 'coated reservoir" refers to a system where the intragranular phase has a core and on it is a coating of the reverse enteric polymer. The term intra-granular phase' is meant to include granules or agglomerates or pellets, that are uncoated or are coated with an alcohol dose-dumping resistance polymer, the coating being considered as a part of the intragranular phase.

The term 'solid dispersion' as intended herein refers to a dispersion wherein the solid state of a drug in solid diluent as determined by X-ray diffract gram compared to a physical of the drug and solid diluent shows that the peaks characteristic of the crystalline drug are reduced or absent. Solid dispersions may also be called solid-state dispersions.

The term 'alcohol dose-dumping resistance polymer' refers to polymers that are generally soluble in water but are insoluble in 40% v/v solution in water used in an amount such that they allow immediate release of the drug in the absence of alcohol but provide improved resistance to alcohol dose-dumping as tested by dissolution in 40% v/v alcohol. Therefore, the term incorporates by definition, use of appropriate amounts.

DETAILED DESCRIPTION OF THE INVENTION

The abuse deterrent immediate release solid dosage form of the present invention comprises a drug susceptible to abuse and a release inhibiting agent wherein the release inhibiting agent is a combination of one or more reverse enteric polymers and an antacid wherein at least one polymer is a reverse enteric polymer. The second polymer may be an alcohol dose-dumping resistance polymer. The alcohol dose-dumping resistance polymer is used in amounts sufficient to prevent alcohol dose-dumping. Dose-dumping resistance of the solid dosage form is tested as illustrated in working Example 6 hereinbelow.

According to the present invention, the drug susceptible to abuse includes, but is not limited to, opioids, central nervous system (CNS) depressants and stimulants. The opioids are usually prescribed to treat pain. Central nervous system depressants are used to treat anxiety and sleep disorders and the stimulants are most often prescribed to treat attention deficit hyperactive disorder (ADHD). Opioids act by attaching to specific proteins called opioid receptors, which are found in the brain, spinal cord, gastrointestinal tract, and other organs in the body. When these drugs attach to their receptors, they reduce the perception of pain. Opioids can also produce drowsiness, mental confusion, nausea, constipation, and, depending upon the amount of drug taken, can depress respiration. Some people experience a euphoric response to opioid medications, since these drugs also affect the brain regions involved in reward. Those who abuse opioids may seek to intensify their experience.

According to the present invention, the drug susceptible to abuse may be an opioid. The opioids are selected from the group consisting of, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tapentadol, tilidine, tramadol, pharmaceutically acceptable salts thereof, and mixtures thereof.

According to the present invention, the drug susceptible to abuse may be central nervous system (CNS) depressants. The central nervous system (CNS) depressants are selected from the group consisting of, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate, amobarbital, aprobarbital, butabarbital, butalbital, methohexital, mephobarbital, metharbital, pentobarbital, phenobarbital, secobarbital, pharmaceutically acceptable salts thereof, and mixtures thereof. According to one embodiment of the present invention, the drugs that cause emergency situations when taken in overdose include, but are not limited to, opioids, central nervous system depressants and stimulants. The opioids are usually prescribed to treat pain. Central nervous system depressants are used to treat anxiety and sleep disorders and the stimulants are most often prescribed to treat attention deficit hyperactive disorder (ADHD). Opioids act by attaching to specific proteins called opioid receptors, which are found in the brain, spinal cord, gastrointestinal tract, and other organs in the body. When these drugs attach to their receptors, they reduce the perception of pain. Opioids can also produce drowsiness, mental confusion, nausea, constipation and depending upon the amount of drug taken, can depress respiration. Some people experience a euphoric response to opioid medications, since these drugs also affect the brain regions involved in reward. Those who abuse opioids may seek to intensify their experience.

Drugs suitable in the present invention include, but are not limited to, drugs whose overdose consumption, can lead to emergency visits, wherein the drugs is prescribed to be consumed by oral administration. The drugs may be selected from the group consisting of, but are not limited to cocaine, heroin, Cannabinoids, Marijuana, Synthetic cannabinoids Stimulants, 3,4-methylenedioxy-N-methylamphetamine (MDMA-Ecstasy), γ-hydroxybutyric acid (GHB), Flunitrazepam (Rohypnol), Ketamine, Lysergic acid diethylamide (LSD). It may be psychotherapeutic agents like antidepressants-monoamio oxidase inhibitors (MOA), phenylpiperazines like nefazodone and trazodone or selective serotonin norepinephrine reuptake Inhibitors (SSNRI) antidepressants like desvenlafaxine, duloxetine, venlafaxine. Other drugs include selective serotonin Reuptake Inhibitors (SSRI) antidepressants such as citalopram, fluoxetine, fluvoxamine, paroxetine and sertraline. Tetracyclic antidepressants (TCA) like maprotiline, mirtazapine, tricyclic antidepressants like amitriptyline, desipramine, doxepin, imipramine, nortriptyline are also suitable drugs according to the present invention. Atypical antipsychotics like bupropion, clozapine, olanzapine, quetiapine and risperidone, phenothiazine antipsychotics like chlorpromazine, fluphenazine, perphenazine, prochlorperazine, thioridazine, triflupromazine are also drugs that are suitable according to the present invention. Other class of drugs include, analgesics, antimigraine agents, cyclooxygenase inhibitors, Opiates, buprenorphine, codeine, dihydrocodeine, fenatyl, hydrocodone, hydromorphone, mepreidine, morphine, oxycodone, pentazocine, phenacetin, propoxyphene. Non-steroidal anti-inflammatory agents like ibuprofen, naproxen, salicylates, aspirin, acetaminophen, tramadol. Anorexiants like phenylpropanolamine. anticonvulsants like barbiturates anticonvulsants, benzodiazepine anticonvulsants, carbamate anticonvulsants, carbonic anhydrase inhibitor anticonvulsants, dibenzazepine anticonvulsants like carbamazepine, oxcarbazepine, rufinamide, fatty acid derivative anticonvulsants like divalproex, sodium valproic acid, gamma-aminobutyric acid analogs like gabapentin, hydantoin anticonvulsants like phenytoin, oxazolidinedione anticonvulsants, pyrrolidine anticonvulsants, succinimide anticonvulsants, triazine anticonvulsants. Antiemetic/antivertigo agents like 5HT3 receptor antagonists, anticholinergic antiemetics, phenothiazine antiemetics. antiparkinson agents like anticholinergic antiparkinson agents like benztropine, dopaminergic antiparkinsonism agents. Other drugs include barbiturates like phenobarbital, benzodiazepines like alprazolam, chlordiazepoxide, clonazepam, clorazepate, diazepam, flurazepam, lorazepam, oxazepam, temazepam, triazolam, misc. anxiolytics, sedatives, and hypnotics like buspirone chloral hydrate, diphenhydramine, doxylamine, hydroxyzine, zolpidem. CNS stimulants like amphetamine, dextroamphetamine, benzphetamine, dextroamphetamine, and methylphenidate. Other class of drugs includes skeletal muscle relaxants like carisoprodol, chlorzoxazone, cyclobenzaprine, metaxalone, methocarbamol tizanidine. cholinergic agonists, cholinesterase inhibitors, expectorants, selective phosphodiesterase-4 inhibitors, antiasthmatic, antitussives, leukotriene modifiers, mast cell stabilizers and mucolytics.

Categories of the drugs, that may be used in the present invention, further includes, centrally acting antiadrenergic agents like clonidine, beta-adrenergic blocking agents, beta blockers like atenolol, propranolol, calcium channel blocking agents, diuretics, carbonic anhydrase inhibitors, loop diuretics, potassium-sparing diuretics thiazide and thiazide-like diuretics, renin Inhibitors, vasopressin antagonists agents for hypertensive emergencies. Aldosterone receptor antagonists, angiotensin converting enzyme inhibitors, angiotensin II inhibitors and antiarrhythmic agents. It also includes drugs like anti-infectives like ameobicides, aminoglycosides, anthelmintics, antifungals like Azole antifungals and echinocandins, polyenes. Antimalarial agents like quinolones. Anti-tuberculosis agents like aminosalicylates, nicotinic acid derivatives, rifamycin derivatives, *streptomyces* derivatives. antiviral agents like adamantane antivirals, antiviral interferons, integrase strand transfer inhibitor, Neuraminidase inhibitors, non-nucleoside reverse-transcriptase inhibitors (NNRTIs), NRTIs, Protease inhibitors, Purine nucleosides. Antibiotics like carbapenems, cephalosporins, glycopeptide antibiotics glycylcyclines, lincomycin derivatives, macrolide derivatives, ketolides, macrolides, penicillins, aminopenicillins, antipseudomonal penicillins, Beta-lactamase inhibitors, Natural penicillins penicillinase resistant penicillins, quinolones, sulfonamides, tetracyclines, and urinary anti-infective. antineoplastics like alkylating agents, Anti-CTLA-4 monoclonal antibodies, antimetabolites antineoplastic antibiotics, antineoplastic hormones, antineoplastic interferons, CD20 monoclonal antibodies, EGFR inhibitors, HER2 inhibitors, histone deacetylase inhibitors, mitotic inhibitors, mTOR inhibitors, VEGF/VEGFR inhibitors. It also includes dugs like coagulation modifiers like anticoagulants, coumarins and indanediones, Factor Xa inhibitors, Heparins, Thrombin inhibitors, Antiplatelet agents, Glycoprotein platelet inhibitors, Platelet aggregation inhibitors, Heparin antagonists, Platelet-stimulating agents, thrombolytics. Gastrointestinal agents like 5-aminosalicylates, Antacids, Anti-diarrheal, digestive enzymes, functional bowel disorder agents, chloride channel activators, peripheral opioid receptor antagonists, Serotoninergic neuroenteric modulators, Gallstone solubilizing agents, GI stimulants, *H. pylori* eradication agents, H2 antagonists Laxatives, Proton pump inhibitors. Genitourinary tract agents, Impotence agents, Tocolytic agents, Urinary antispasmodics, Urinary pH modifiers, uterotonic agents. Hormones like 5-Alpha-reductase inhibitors, adrenal cortical steroids like corticotropin, glucocorticoids, mineralocorticoids, adrenal corticosteroid inhibitors, antidiuretic hormones, anti-gonadotropic agents, anti-thyroid agents, calcitonin, gonadotropin-releasing hormone antagonists, growth hormone receptor blockers, growth hormones, insulin-like growth factor, parathyroid hormone and analogs, progesterone receptor modulators, prolactin inhibitors, selective estrogen receptor modulators, sex hormones androgens and anabolic steroids, contraceptives, Estrogens, gonadotropin-releasing hormone and analogs gonadotropins, progestins, sex hormone combinations, somatostatin and somatostatin analogs, synthetic ovulation stimulants, thyroid hormones. Immunologic agents like immune globulins, immunostimulants, Bacterial vaccines, colony stimulating factors. interferons, immunosuppressive agents, calcineurin inhibitors, Interleukin inhibitors, Selective immunosuppressants, TNF alfa inhibitors metabolic agents like antidiabetic agents, Alpha-glucosidase inhibitors, Amylin analogs, Antidiabetic combinations like Dipeptidyl peptidase 4 inhibitors, Insulin, meglitinides, biguanides, sulfonylureas, thiazolidinediones, antigout agents, antihyperlipidemic agents, antihyperlipidemic combinations. Other classes of drugs further include bile acid sequestrants, cholesterol absorption inhibitors, Fibric acid derivatives, HMG-CoA reductase inhibitors, antihyperuricemic agents, bone resorption inhibitors, bisphosphonates, glucose elevating Agents, lysosomal enzymes, Peripherally acting antiobesity agents and miscellaneous metabolic agents.

Antipsoriatics, Antirheumatics, chelating agents, cholinergic muscle stimulants, psoralens, smoking cessation agents. radiologic agents like radio-contrast agents, and radiopharmaceuticals According to the present invention, the drugs that cause emergency situations when taken in overdose may be central nervous system depressants. The central nervous system depressants are selected from the group consisting of, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate, amobarbital, aprobarbotal, butabarbital, butalbital, methohexital, mephobarbital, metharbital, pentobarbital, phenobarbital, secobarbital.

According to the present invention, the drug susceptible to abuse may be central nervous system (CNS) stimulants. The central nervous system (CNS) stimulants are selected from the group consisting of, but are not limited to, amphetamines, dextroamphetamine, methamphetamine, methylphenidate, pharmaceutically acceptable salts thereof and mixtures thereof.

The "reverse enteric polymer" used in the solid dosage form of the present invention is a polymer that is soluble in acidic solutions but is insoluble or alternatively gels above a second higher pH value.

In several of the embodiments, as herein described, the reverse enteric polymer functions as a release rate controlling polymer above a critical pH but has little rate controlling ability below the critical pH. Examples are found in polymers that have group capable of accepting the hydrogen ion from an acid below the critical pH and thus becoming soluble in acid environment and fall under the class of pH dependent polymers. The reverse enteric polymer used is selected from polymers that are prepared by polymerizing a mixture of the hydrophobic and basic monomer or a mixture of the hydrophobic, hydrophilic and basic monomer wherein the basic monomer may be selected from the group consisting of dimethyl amino ethyl acrylate, diethyl amino ethyl ethacrylate, diethyl amino ethyl acrylate, piperidine ethyl methacrylate and 2-tert-butyl amino ethyl methacrylate.

An example of a preferred reverse enteric polymer i.e a pH dependent polymer used is a methyl methacrylate butyl methacrylate-dimethyl aminoethyl methacrylate copolymer which is a cationic copolymer synthesized from dimethyl aminoethyl methacrylate and neutral methacrylic acid esters, more particularly as is commercially available under the trade name Eudragit™ E which is soluble at an acidic pH such as pH 5 and swellable and permeable above a higher pH such as above pH 5. It is depicted by the following structure.

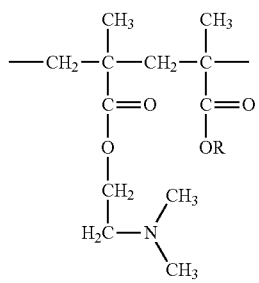

R = CH₃, C₄H₉

The repeating unit in the polymer has the following structure: where R represents $CH_3$ and $C_4H_9$ groups and the polymer has a molecular weight about 1,50,000. They may exist in different physical forms. The Eudragit™ E 100 product is granular, the Eudragit™ E 12.5 product is a 12.5% solution of E 100 in isopropanol and acetone, and the Eudragit EPO product is a fine powder made from E 100. Various grades of this polymer are commercially available from Evonik, Germany. The amount of Eudragit™ E in the present invention varies from 0.5% to about 30% by weight of the dosage form, preferably about 2% to about 30% by weight of the dosage form, more preferably about 5% to about 20% by weight of the solid dosage form. The ratio of weight of polymer to the weight of drug varies from 0.5 to about 8.0, preferably about 3.0 to about 8.0, more preferably about 6.8. The amount of this reverse enteric polymer may be expressed in terms of its weight ratio. The embodiments having coated reservoir type i.e when the reverse enteric polymer is coated on the drug susceptible to abuse or on the core containing the drug, i.e. it is not in admixture with the drug, release inhibition on multiple pill administration is controlled more effectively and thus the weight ratio of methacrylate-dimethyl aminoethyl methacrylate copolymer to the drug is about 1 or less than 1.0, preferably, about 0.5.

Other suitable examples of such pH dependent polymers may be found in the art. It is beneficial to use polymers which are soluble only at pH 5.5 or below, that are additionally also impermeable since this further helps control the dissolution rate. In more preferred embodiments, the reverse enteric polymer is selected from a polymer that is soluble below about pH 5.0 but insoluble above about pH 5.5 For example, US20050137372 disclosed similar polymers prepared by polymerizing a mixture of the hydrophobic and basic monomer or a mixture of the hydrophobic, hydrophilic and basic monomer wherein the basic monomer may be selected from the group consisting of dimethyl amino ethyl acrylate, diethyl amino ethyl ethacrylate, diethyl amino ethyl acrylate, piperidine ethyl methacrylate and 2-tert-butyl amino ethyl methacrylate. Several other polymers having basic functional groups and thus the desired pH dependent solubility behavior can be used according to the present invention. Poly(lysine) (PL), poly(ethylenimine) (PEI) and chitosan are examples of such polymers.

The reverse enteric polymer used in the solid dosage form of the present invention may be used in the form of a dispersion or in a powder form for preparation of the solid dosage form.

It is thus within skill in the art to use existing polymers with the appropriate basic ionizable groups or to synthesize new such polymers by incorporating monomers having basic ionizable groups and any such polymer may be used according to the scope of the present invention.

Suitable examples of the reverse enteric polymer that is soluble at an acidic pH but is insoluble at a second higher pH value, include, but are not limited to, methyl methacrylate and diethylaminoethyl methacrylate and the like. Any other reverse enteric polymer having such properties is encompassed within the scope of the this embodiment of the present invention. In one specific preferred embodiment, the reverse enteric polymer that can be utilized in the present invention is a copolymer comprising amino and/or alkylamino and/or dialkyl amino groups such as copolymers comprising methyl methacrylate and diethylaminoethyl methacrylate such as commercially available as Kollicoat® Smartseal 30 D from BASF. The polymer has a molecular weight of about 200,000 and a glass transition temperature of 57 to 63° C. The ratio of methyl methacrylate and diethylaminoethyl methacrylate to the drug susceptible to abuse may vary depending upon the solubility and the dose of the drug, present in each unit and is significantly lower when the reverse enteric polymer is used to form a coating surrounding a core containing the drug susceptible to abuse i.e in the coated reservoir type of embodiments according to the present invention. Therefore coating of the reverse enteric polymer is a preferred and more efficient method for preparing solid dosage forms of the present invention and imparting the improved release inhibition when multiple pills are ingested by the abuse.

Thus, in one aspect of abuse deterrent immediate release solid dosage form of the present invention comprises a drug susceptible to abuse and a release inhibiting agent wherein the release inhibiting agent is a combination of polymer and an antacid wherein the antacid is an alkalizer and further wherein at least one polymer is a reverse enteric polymer and functions as a release rate controlling polymer above a specific pH but has little rate controlling ability below the critical pH. Alternatively, the antacid may be a substance that suppresses gastric acid secretion, for eg., a $H_2$-antagonist.

The term "alkalizer" as used herein refers to physiologically acceptable substances that neutralize acid. Examples of alkalizer include, but are not limited to calcium carbonate, disodium hydrogen phosphate, trisodium orthophosphate, sodium hydroxide, sodium carbonate, potassium hydroxide, sodium bicarbonate, dipotasium carbonate, tromethamine, aluminum trihydroxide, magnesium dihydroxide, aluminium oxide, magnesium oxide and mixture thereof. The amount of alkalizer used in a single unit is selected so that it will not be sufficient to raise the stomach pH to above a critical pH for example 5 or neutral pH; but when more than the prescribed number of units are administered, it is sufficient to raise the pH of the stomach to above the critical pH. Usually the amount of alkalizer in when more than the prescribed number of units should at least raise the pH of 500 ml of 0.01 N HCl to above the critical pH, preferably the amount should be greater and raise the pH of 1000 ml of 0.01N HCl to above the critical pH, and more preferably it may exceed that amount sufficiently to neutralize any immediate rebound secretion of acidic gastric fluids in response to the alkalizer. The amount of alkalizer in one single unit is however selected so that it does not raise the pH of 500 ml, preferably 1000 ml of 0.01N HCl to above the critical pH so that when a single unit is orally administered the polymer does not behave like a rate controlling polymer but when more than the prescribed number of units are administered, it behaves like a rate controlling polymer and inhibits release.

The coated reservoir solid dosage form of the present invention may include a second polymer which is an alcohol dose-dumping resistance polymer. These polymers may be insoluble in water but are insoluble in 40% v/v solution of alcohol in water. These polymers may be incorporated either in intragranular phase or extragranular phase and provide improved resistance to alcohol dose dumping and at the same time they do not slow down the rate of release of the drug when in the absence of alcohol allowing the dosage form to perform as an immediate release dosage form. Examples of such polymers include, but are not limited to, polyvinyl alcohol, polyethylene oxide, sodium starch glycolate and the like and mixture thereof. The polymers that do not affect or control the release of the drug from the immediate release dosage form are suitable to be incorporated into the abuse deterrent immediate release solid dosage form according to the present invention.

The coated reservoir solid dosage form may be fabricated into a suitable form such as sachets, capsules or tablet by methods known in the art and using conventional excipients known in the art such as diluents or fillers, binders, disintegrants, stabilisers glidants, lubricants, surfactants, solubilizing agents, preservatives, coloring agents and others as may be necessitated by the drug to be incorporated in the dosage form. In one specific embodiment, the inventors found that certain disintegrants exhibit reduced swelling power in alcoholic solutions but show very good swelling and disintegration effect in aqueous medium that are devoid of alcohol. Such type of disintegrants is preferable. These type of disintegrants, not only provide resistance to tampering by extracting with alcohol, but help in avoiding dose dumping when the solid dosage form is ingested with alcohol or alcoholic beverages. Examples of such disintegrants include, but are not limited to, sodium starch glycolate, polacrillin potassium and the like and mixtures thereof.

Various embodiments of coated reservoir systems according to the present invention are explained in great details hereinafter.

In certain embodiments of the abuse deterrent immediate release coated reservoir solid dosage form comprises a drug susceptible to abuse and a release inhibiting agent, the release inhibiting agent consisting of a combination of at least two polymers and an antacid wherein at least one first polymer is a reverse enteric polymer and at least one second polymer is an alcohol dose-dumping resistance polymer wherein the reverse enteric polymer, alcohol dose-dumping resistance polymer and the antacid are present in amounts such that when more than the prescribed number of units, such as two or more number of units, of the dosage form are tested for in-vitro dissolution in 500 ml of an acidic medium such as for example, 0.01N HCl, by USP dissolution method, the release is inhibited as compared to the immediate release of the prescribed number of units, such as, for example, at least 80±5% of drug in a single prescribed unit of the dosage form in one hour. In one example, 0.01 HCL with 40% ethanol by volume was used as a dissolution medium. The in vitro dissolution was conducted in Type II, USP apparatus, rotating at a speed of 50 rpm. Certain embodiments may also have a polymer incorporated in a manner to provide tamper resistance.

The reverse enteric polymer and the antacid together function as the release inhibiting agent. The amount and the ratios of the reverse enteric polymer to the antacid can vary from 1:100 to 1:20, preferably, it may range from about 1:80 to about 1:50. The amounts and ratios can be determined as exemplified in the examples and amounts that function to allow immediate release when only one single unit of the dosage form are used but function as release inhibiting agent when multiple units are used may be determined and may vary depending on the Type of system involved and the choice of the reverse enteric polymer and the antacid. It may be noted that amount of the antacid as well as its ionization capacity determines how much the release can be inhibited from the more than the prescribed number of units, for instance, in this case, it was found that when a combination of sodium bicarbonate and magnesium oxide were used, about 25% by weight of the dosage form was found not to inhibit the release from 2 units, but when more than 2 units were subjected to dissolution, the release was inhibited. In the cases where the antacid is a combination of sodium bicarbonate and magnesium oxide, at a concentration of about 30% by weight of the solid dosage form was found to provide inhibition when two units were tested. In this case, therefore, the immediate release solid dosage form can be designed to incorporate the unit dose of the drug, in a single unit. This shows that the immediate release dosage form of the present invention can be altered as per the need of the number of units at which inhibition is desired.

According to another embodiment of the present invention, abuse deterrent immediate release solid dosage form of the present invention comprises a drug susceptible to abuse and a release inhibiting agent wherein the release inhibiting agent is a combination of reverse enteric polymer and an antacid and wherein the reverse enteric polymer functions as a release rate controlling polymer above a critical pH but has little rate controlling ability below the critical pH and wherein the drug and first part of the polymer may be present in admixture and form a core which is coated with a second part of the polymer and the antacid is present in external phase outside the coated core (The coated reservoir type).

The coated reservoir systems according to the present invention can be sub divided into Type I, Type II, Type III, Type IV, Type V, Type VI, Type VII, Type VIII, Type IX, Type X, Type XI, Type XII, Type XIII, Type XIV, Type XV, Type XIV and Type XVII.

Figure 1:
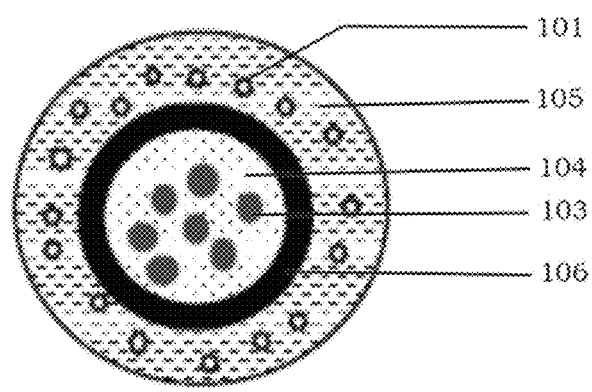
FIG. 1 depicts an Abuse Deterrent Immediate Release Solid dosage form of Coated Reservoir System Type I with an intragranular phase having a core containing the drug and a coating containing reverse enteric polymer, the coated core forming an intragranular phase and an antacid such as alkalizer in the extragranular phase.

Type I as depicted in FIG. 1 refers to an Abuse Deterrent Immediate Release Solid dosage form of Coated Reservoir System Type I with an intragranular phase having a core containing the drug and a coating containing reverse enteric polymer, the coated core forming an intragranular phase and an antacid such as alkalizer in the extragranular phase.

Figure 2:
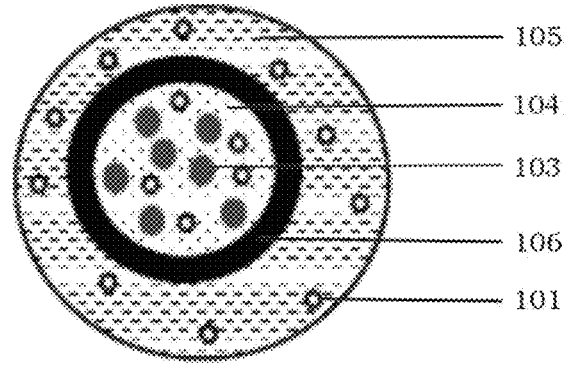
FIG. 2 depicts an Abuse Deterrent Immediate Release Solid dosage form of Coated Reservoir System Type II having a core containing the drug and a part of the antacid such as alkalizer and a coating containing reverse enteric polymer, the coated core forming an intragranular phase; and an antacid such as alkalizer in the extragranular phase.

Type II as depicted in FIG. 2 refers to an Abuse Deterrent Immediate Release solid dosage form of Coated Reservoir System Type II having a core containing the drug and a part of the antacid such as alkalizer and a coating containing reverse enteric polymer, the coated core forming an intragranular phase; and an antacid such as alkalizer in the extragranular phase.

Figure 3:
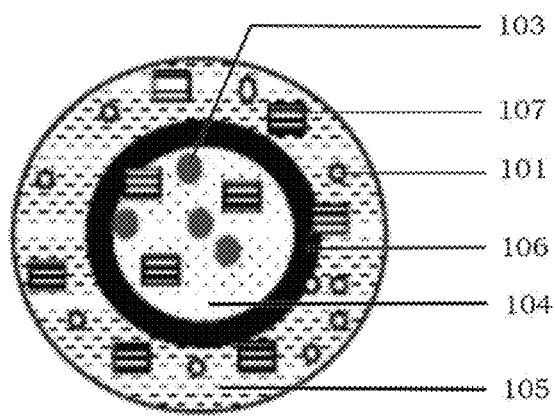
FIG. 3 depicts an Abuse Deterrent Immediate Release Solid dosage form of Coated Reservoir System Type III having a core containing the drug and a second polymer wherein the second polymer is an alcohol dose-dumping resistance polymer and a coating containing reverse enteric polymer, the coated core forming an intragranular phase; and an antacid such as alkalizer and a second polymer, which is an alcohol dose-dumping resistance polymer, forming an extragranular phase.

Type III as depicted in FIG. 3 refers to Abuse Deterrent Immediate solid dosage form of coated reservoir system Type III having a core containing the drug and an alcohol dose-dumping resistance polymer and a coating containing reverse enteric polymer, the coated core forming an intragranular phase; and an antacid such as alkalizer and an alcohol dose-dumping resistance polymer, forming an extragranular phase.

Figure 4:
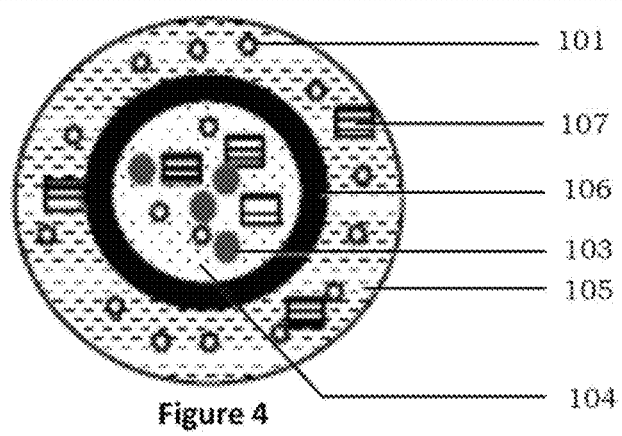
FIG. 4 depicts an Abuse Deterrent Immediate Release Solid dosage form of Coated Reservoir System Type IV having a core containing the drug, a part of the antacid such as alkalizer and a second polymer which is an alcohol dose-dumping resistance polymer and is coated with a reverse enteric polymer; the coated core forming an intragranular phase and an antacid such as alkalizer and the second polymer which is an alcohol dose-dumping resistance polymer, forming an extragranular phase.

Type IV as depicted in FIG. 4 refers to an Abuse Deterrent Immediate Release solid dosage form of coated reservoir system Type IV having a core containing the drug, alcohol dose-dumping resistance polymer and part of the antacid and is coated with a reverse enteric polymer; the coated core forming an intragranular phase and a part of the antacid such as alkalizer and part of the alcohol dose-dumping resistance polymer, forming an extragranular phase.

Figure 5:
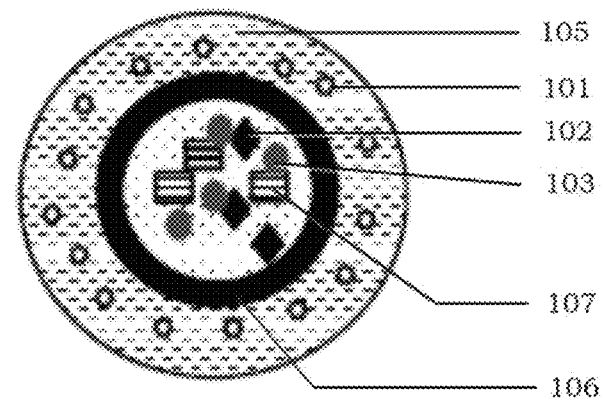
FIG. 5 depicts an Abuse Deterrent Immediate Release Solid dosage form of Coated Reservoir System Type V having a core containing the drug, reverse enteric polymer and second polymer which is an alcohol dose-dumping resistance polymer and a coating containing reverse enteric polymer, the coated core forming an intragranular phase and an antacid such as alkalizer in the extragranular phase.

Type V as depicted in FIG. 5 refers to an Abuse Deterrent Immediate solid dosage form of Coated Reservoir System Type V having a core containing the drug, a part of the reverse enteric polymer and an alcohol dose-dumping resistance polymer and a coating containing reverse enteric polymer, the coated core forming an intragranular phase and an antacid such as alkalizer in the extragranular phase.

Figure 6:
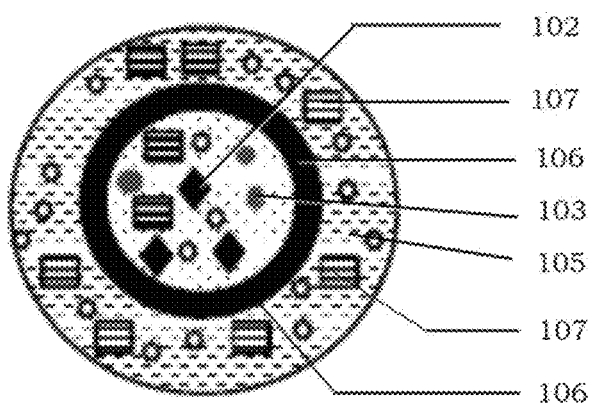
FIG. 6 depicts an Abuse Deterrent Immediate Release Solid dosage form of Coated Reservoir System type VI having a core containing drug, reverse enteric polymer, part of the antacid such as alkalizer and a second polymer which is an alcohol dose-dumping resistance polymer, the core is coated with reverse enteric polymer, the coated core forming an intragranular phase and the second polymer which is an alcohol dose-dumping resistance polymer and part of the antacid such as alkalizer, forming an extragranular phase.

Type VI as depicted in FIG. 6 refers to an Abuse Deterrent Immediate Release solid dosage form of Coated Reservoir System Type VI having a core containing drug, reverse enteric polymer, part of the antacid and an alcohol dose-dumping resistance polymer, the core is coated with reverse enteric polymer, the coated core forming an intragranular phase and a part of the antacid such as alkalizer and an alcohol dose-dumping resistance polymer forming an extragranular phase.

Figure 7:
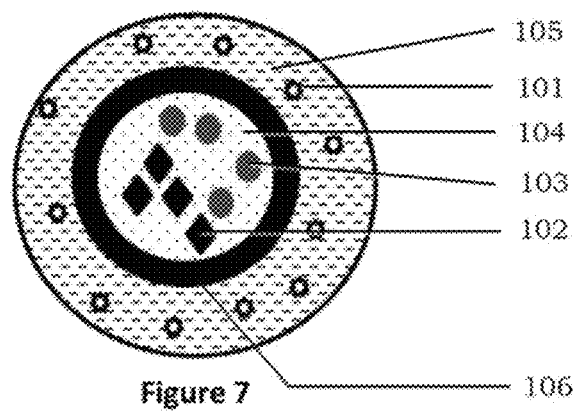
FIG. 7 depicts an Abuse Deterrent Immediate Release Solid dosage form of Coated Reservoir System type VII having a core containing drug, reverse enteric polymer, the core is coated with reverse enteric polymer, coated core forming an intragranular phase and an antacid such as alkalizer in the extragranular phase.

Type VII as depicted in FIG. 7 refers to an Abuse Deterrent Immediate Release solid dosage form of Coated Reservoir System Type VII having a core containing drug, a part of the reverse enteric polymer, the core is coated with part of the reverse enteric polymer, coated core forming an intragranular phase and an antacid such as alkalizer in the extragranular phase.

Figure 8:
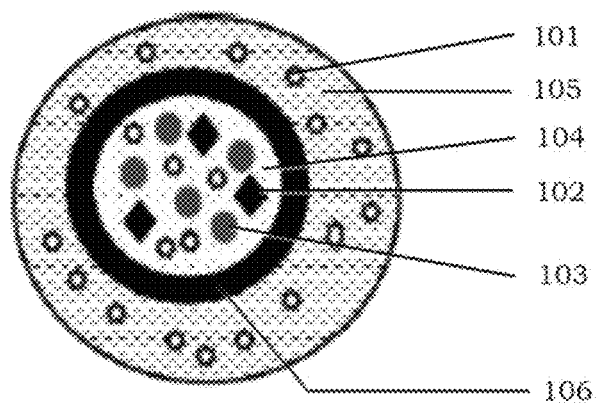
FIG. 8 depicts an Abuse Deterrent Immediate Release Solid dosage form of Coated Reservoir System type VIII a core containing drug, reverse enteric polymer and antacid such as alkalizer, the core is coated with reverse enteric polymer, the coated core forming an intragranular phase and an antacid such as alkalizer in the extragranular phase.

Type VIII as depicted in FIG. 8 refers to an Abuse Deterrent Immediate Release Solid dosage form of Coated Reservoir System Type VIII a core containing drug, reverse enteric polymer and antacid such as alkalizer, toe core is coated with reverse enteric polymer, the coated core forming an intragranular phase and an antacid such as alkalizer in the extragranular phase.

Figure 9:
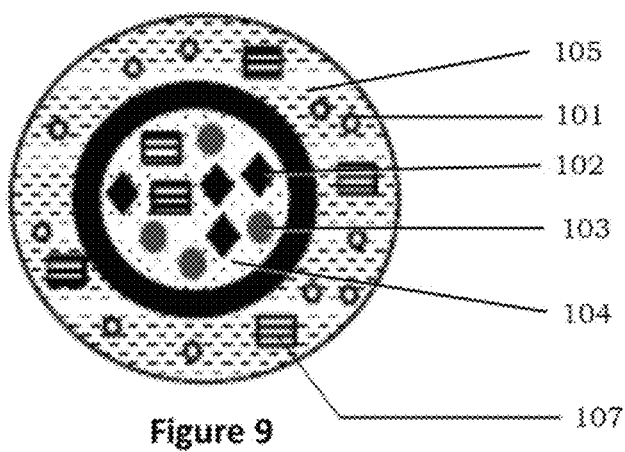
FIG. 9 depicts an Abuse Deterrent Immediate Release Solid dosage form of Coated Reservoir System type IX a core containing drug, part of the reverse enteric polymer and second polymer which is an alcohol dose-dumping resistance polymer, the core is coated with remaining part of the reverse enteric polymer, the coated core forming an intragranular phase and an antacid such as alkalizer and a second polymer which is an alcohol dose-dumping resistance polymer, forming an extragranular phase.

Type IX as depicted in FIG. 9 refers to an Abuse Deterrent Immediate Release Solid dosage form of Coated Reservoir System Type IX a core containing drug, part of the reverse enteric polymer and a part of the alcohol dose-dumping resistance polymer, the core is coated with remaining part of the reverse enteric polymer, the coated core forming an intragranular phase and an antacid such as alkalizer and part of the alcohol dose-dumping resistance polymer, forming an extragranular phase.

Figure 10:
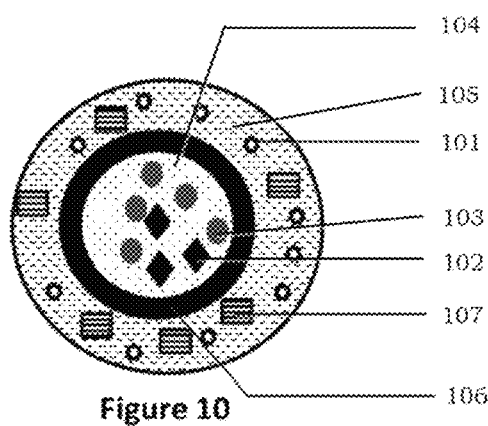
FIG. 10 depicts an Abuse Deterrent Immediate Release Solid dosage form of Coated Reservoir System type X having a core containing drug, part of the reverse enteric polymer, the core is coated with remaining part of the reverse enteric polymer, the coated core forming an intragranular phase and an antacid such as alkalizer and second polymer which is an alcohol dose-dumping resistance polymer, forming an extragranular phase.

Type X as depicted in FIG. 10 refers to an Abuse Deterrent Immediate Release Solid dosage form of Coated Reservoir System Type X having a core containing drug, part of the reverse enteric polymer, the core is coated with remaining part of the reverse enteric polymer, the coated core forming an intragranular phase and an antacid such as alkalizer and an alcohol dose-dumping resistance polymer, forming an extragranular phase.

Figure 11:
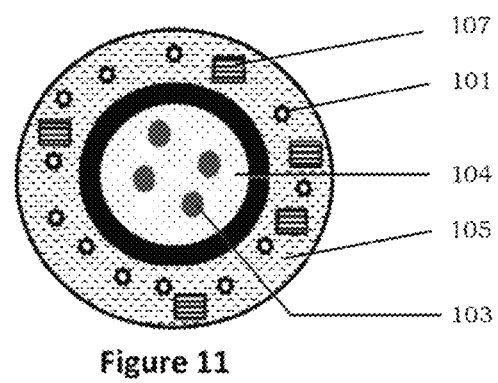
FIG. 11 depicts an Abuse Deterrent Immediate Release Solid dosage form of Coated Reservoir System type XI having a core containing drug, coated with reverse enteric polymer, the coated core forming an intragranular phase and an antacid such as alkalizer and second polymer which is an alcohol dose-dumping resistance polymer, forming an extragranular phase.

Type XI as depicted in FIG. 11 refers to an Abuse Deterrent Immediate Release Solid dosage form of Coated Reservoir System Type XI having a core containing drug, coated with reverse enteric polymer, the coated core forming an intragranular phase and an antacid such as alkalizer and an alcohol dose-dumping resistance polymer, forming an extragranular phase.

Figure 12:
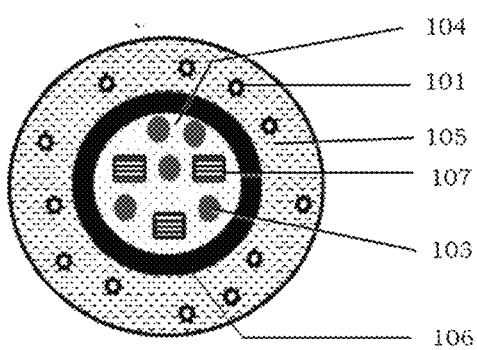
FIG. 12 depicts an Abuse Deterrent Immediate Release Solid dosage form of Coated Reservoir System type XII having a core containing drug and second polymer which is an alcohol dose-dumping resistance polymer, the core is coated with reverse enteric polymer, coated core forming an intragranular phase and an antacid such as alkalizer in the extragranular phase.

Type XII as depicted in FIG. 12 refers to an Abuse Deterrent Immediate Release Solid dosage form of Coated Reservoir System Type XII having a core containing drug and an alcohol dose-dumping resistance polymer, the core is coated with reverse enteric polymer, coated core forming an intragranular phase and an antacid such as alkalizer in the extragranular phase.

Type XIII as depicted in FIG. 13 refers to an Abuse Deterrent Immediate Release Solid dosage form of Coated Reservoir System Type XIII having a core containing drug, part of the antacid such as alkalizer and an alcohol dose-dumping resistance polymer, the core is coated with reverse enteric polymer, the coated core forming an intragranular phase and a remaining part of the antacid such as alkalizer forming an extragranular phase.

Type XIV as depicted in FIG. 14 refers to an Abuse Deterrent Immediate Release Solid dosage form of Coated Reservoir System Type XIV having a core containing drug, part of the antacid such as alkalizer and part of the reverse enteric polymer, the core is coated with part of the reverse enteric polymer, the coated core forming the intragranular phase and a part of the antacid such as alkalizer and an alcohol dose-dumping resistance polymer, forming an extragranular phase.

Figure 15:
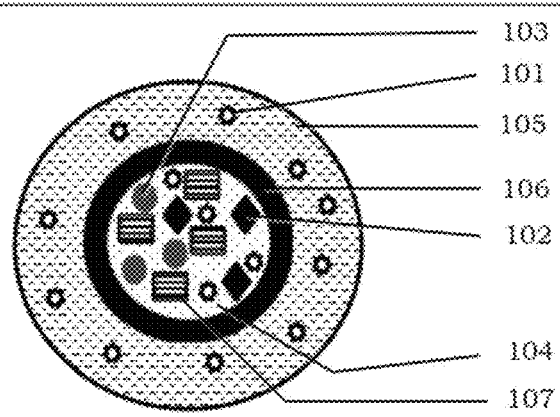
FIG. 15 depicts an Abuse Deterrent Immediate Release Solid dosage form of Coated Reservoir System type XV having a core containing drug, second polymer which is an alcohol dose-dumping resistance polymer, a part of antacid such as alkalizer and part of the reverse enteric polymer, the core is coated with part of the reverse enteric polymer, the coated core forming an intragranular phase and remaining part of the antacid such as alkalizer in the extragranular phase.

Type XV as depicted in FIG. 15 refers an Abuse Deterrent Immediate Release Solid dosage form of Coated Reservoir Immediate Release Solid dosage form of Coated Reservoir System Type XV having a core containing drug, an alcohol dose-dumping resistance polymer, a part of antacid such as alkalizer and part of the reverse enteric polymer, the core is coated with part of the reverse enteric polymer, the coated core forming an intragranular phase and remaining part of the antacid such as alkalizer in the extragranular phase.

Figure 16:
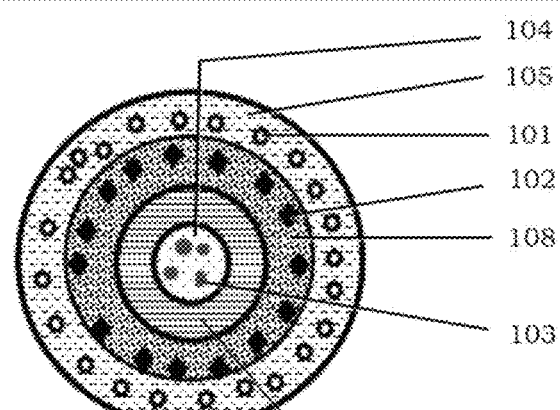
FIG. 16 depicts an Abuse Deterrent Immediate Release Solid dosage form of Coated Reservoir System type XVI having a core containing drug is coated with a second polymer which is an alcohol dose-dumping resistance polymer, the coated core is further coated with a coating containing reverse enteric polymer and water insoluble polymer, coated core forming an intragranular phase and an antacid such as alkalizer in the extragranular phase.

Type XVI as depicted in FIG. 16 refers to an Abuse Deterrent Immediate Release Solid dosage form of Coated Reservoir System Type XVI having a core containing drug is coated with a alcohol dose-dumping resistance polymer, the coated core is further coated with a coating containing reverse enteric polymer and water insoluble polymer, coated core forming an intragranular phase and an antacid such as alkalizer in the extragranular phase.

Figure 17:
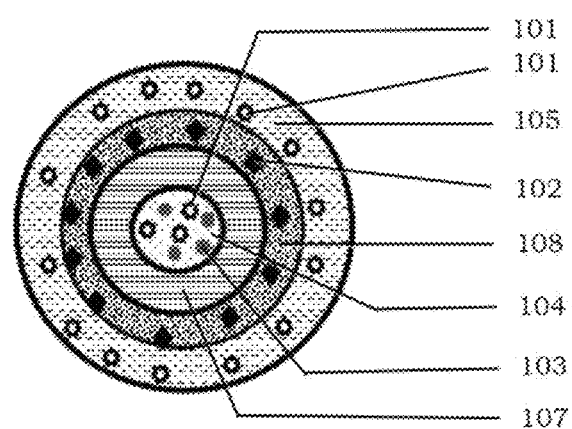
FIG. 17 depicts an Abuse Deterrent Immediate Release Solid dosage form of Coated Reservoir System type XVII having a core containing drug and part of the antacid such as alkalizer, the core is coated with a second polymer which is an alcohol dose-dumping resistance polymer, the coated core is further coated with a coating containing reverse enteric polymer and water insoluble polymer, the coated core forming an intragranular phase and the remaining part of the antacid such as alkalizer forming in the extragranular phase.

Type XVII as depicted in FIG. 17 refers to an Abuse Deterrent Immediate Release Solid dosage form of Coated Reservoir System XVII having a core containing drug and part of the antacid such as alkalizer, the core is coated with an alcohol dose-dumping resistance polymer, the coated core is further coated with a coating containing reverse enteric polymer and water insoluble polymer, the coated core forming an intragranular phase and the remaining part of the antacid such as alkalizer forming in the extragranular phase.

As dosage forms intended for quick onset of action are given a number of times a day as compared to slow release forms that are given at a lower frequency for example once-a-day, they contain a lower amount of drug than in the extended release form. An abuser will want to receive higher amounts by taking multiple units. Therefore, the percent of prescribed dose that an abuser will release at 30 min and 60 min for absorption by taking multiple units of the dosage form was calculated. The prescribed dose is the amount contained in a single unit of the dosage form. Table 1 shows the results for Examples 1 and 2.

The results demonstrated that the coated reservoir type system can be formulated such that when a patient takes a single unit he will release the desired single dose of the drug in 30 to 60 minutes for quick onset of action but the abuser will not succeed in achieving a release of more than about 1.5 times the prescribed dose at 30 min by orally administering three units of the dosage form. Preferred Example 2 further demonstrates that the coated reservoir type system can be formulated such that absorption greater than about 1.5 times the prescribed dose is not achieved even at 60 minutes.

In one particular embodiment, the intragranular phase is prepared by wet granulation. These granules are mixed with the extragranular ingredients and can be converted into a tablet by compression or the phases may be mixed and filled into hard gelatin capsules. The amount of reverse enteric polymer used for the coating is present in the range of around 7% to 10%. The granules of the present embodiment are made by the wet granulation technique.

According to another embodiment of the present invention, abuse deterrent solid dosage form of the present invention comprises a drug susceptible to abuse and a release inhibiting agent wherein the release inhibiting agent is a combination of polymer and an antacid and wherein the polymer functions as a release rate controlling polymer above a critical pH but has little rate controlling ability below the critical pH and wherein the drug may be present in a core which is coated with the polymer and the antacid is present in external phase outside the coated core (The coated reservoir type). In this embodiment, the drug susceptible to abuse is mixed with conventional excipients and granulated. Preferably the granulation is achieved by extrusion and spheronization to form spherical pellets suitable for coating. The granules or spherical pellets are coated with a coating composition comprising the polymer. The coated pellets or granules are mixed with a composition comprising an antacid and filled into capsules.

Embodiments of the solid dosage form of the coated reservoir type were tested for in-vitro dissolution in 500 ml, 0.01N HCl, in Type II USP apparatus (Paddle) rotating at a speed of 50 rpm. Illustrative examples 1 and 2 were prepared and accordingly tested. The results are shown in Tables 1 and 2 and in FIG. 1.

In one particular embodiment, the reverse enteric polymer is present in admixture with the drug in an internal phase and the antacid is present in an external phase.

According to one aspect, the present invention provides an abuse deterrent immediate release coated reservoir solid dosage form comprising: a drug susceptible to abuse and a release inhibiting agent, the release inhibiting agent consisting of a combination of at least two polymers and an antacid wherein at least one first polymer is a reverse enteric polymer and at least one second polymer is alcohol dose-dumping resistance polymer, wherein the reverse enteric polymer and the antacid such as alkalizer are present in amounts such that when more than the prescribed number of units of the dosage form are tested for in-vitro dissolution in 500 ml, of an acidic medium by USP dissolution method, the release is inhibited as compared to the immediate release of drug from a single or prescribed number of units in 2 hours when a single or prescribed number of units, of the dosage form is tested. The amount of reverse enteric polymer present in the current embodiment is from about 0.5% to about 5% by weight of the coated reservoir solid dosage form. The amount of antacid present extragranularly ranges from about 20% to 80%, preferably 40% to 70% by weight of the solid dosage form. The alcohol dose-dumping resistance polymer either present intragranularly or extragranularly, can vary from about 0.5% to 15%, preferably 2% to 10% by weight of the solid dosage form. In certain embodiments, the intragranular phase comprises part of the reverse enteric polymer and the drug susceptible to abuse in the form of hot melt extrudates and the part of the reverse enteric polymer is coated onto these extrudates. This embodiment is particularly useful in cases where the reverse enteric polymer to drug ratio is required to be minimal at the same time some amount of reverse enteric polymer is required so as to form the solid dispersion or particularly, solid solution and the remaining amount of the reverse enteric polymer is required as a part of the release inhibiting agent. In certain embodiments, however, the drug may be simply coated with the reverse enteric polymer and then mixed with the antacid which is an alkalizer.

In another embodiment, the reverse enteric polymer, the alcohol dose-dumping resistance polymer and antacid are present in admixture with the drug in the intragranular phase. The antacid component in the present embodiment is also present in the extragranular phase. In this embodiment, the amount of reverse enteric polymer can vary from about 0.5% to about 15%, the amount of alcohol dose-dumping resistance polymer can vary from about 1.0% to 5%, preferably, about 1% to 3% by weight of the solid dosage form. In this embodiment, the reverse enteric polymer is present in a range of about 19 to 67% of the intragranular phase. The alcohol dose-dumping resistance polymer is present in a range of about 4 to 14% of the intragranular phase. The antacid present intragranularly is in a range of about 1 to 9% and the antacid present extragranularly is in a range of about 50% to 55% by weight.

According to one specific embodiment, the abuse deterrent immediate release coated reservoir solid dosage form is resistant to alcohol. That is, the dosage form does not increase the release rate when concomitantly administered with alcohol or alcoholic beverages and preferably, provides reduced rate of release in alcoholic medium as compared to non-alcoholic medium, when tested using standard in vitro dissolution testing methods. In one embodiment dosage form comprises a drug susceptible to abuse and a release inhibiting agent, the release inhibiting agent consisting of a combination of at least two polymers and an antacid present intragranularly wherein at least one first polymer is a reverse enteric polymer and at least one second polymer is alcohol dose-dumping resistance polymer. In this embodiment the alcohol dose-dumping resistance polymer and antacid are also present extragranularly. The range of alcohol dose-dumping resistance polymer present intragranularly ranges from about 4 to 5% and the alcohol dose-dumping resistance polymer present extragranularly ranges from about 12 to 16%. The reverse enteric polymer present in this embodiment ranges from about 19 to 20%. The antacid present intragranularly ranges from about 2 to 3% and the antacid present extragranularly ranges from about 32 to 49%. The granules of the present embodiment are prepared by hot melt extrusion and spheronization technique.

It was found that incorporation of the antacid in the intragranular phase and the extragranular phase provided various advantages such as below:

1. The amount of antacid in the extragranular phase that is required to provide the multiple pill abuse resistance was considerably lower when compared with the solid dosage form that is devoid of an antacid in the intragranular phase, but present only in the extragranular phase.

2. The solid dosage form according to these embodiment of Type II, Type IV, Type VI, type VIII, type XIII, Type XIV, Type XV and type XVII and were found to be resistant to abuse by nasal route and tampering by various mediums used by abuser such as acidic and alcoholic beverages and the like, as compared to embodiments of Type I, Type III, Type V, Type VII, Type IX, Type X, type XI, Type XII, Type XVI.

According to another aspect, the present invention provides an abuse deterrent immediate release coated reservoir solid dosage form comprising:

a drug susceptible to abuse and a release inhibiting agent, the release inhibiting agent consisting of a combination of at least two polymers and an antacid wherein at least one first polymer is a reverse enteric polymer, and at least one second polymer is alcohol dose-dumping resistance polymer, wherein the reverse enteric polymer and the antacid are present in amounts such that when more than two units of the dosage form are tested for in-vitro dissolution in 500 ml, of 0.01N HCl, Type II USP apparatus (Paddle) rotating at a speed of 50 rpm, the release is inhibited as compared to the immediate release of drug from a single units in 2 hours when a single unit of the dosage form is tested.

In another embodiment, drug is present in a solid core and the reverse enteric polymer forms a coat surrounding the solid core and the antacid is present in external phase outside the coated solid core. When the antacid is present in the external phase and the drug is in admixture with the reverse enteric polymer to form an internal phase, then the amount of antacid can vary from about 15 to 60%, preferably, 25 to 50% by weight of the solid dosage form. However, when the reverse enteric polymer is coated on the drug to form an internal phase, the amount of antacid present in the external phase, can vary from about 65% or more, preferably, 75% by weight of the solid dosage form. In certain embodiments, the internal phase constitutes the combination of the reverse enteric polymer and a part of the antacid and the external phase contains other part of the antacid, then the amount of antacid in the internal phase can vary from about 1 to 5% by weight and the amount of antacid present in the external phase can vary from about 10% to 40%, preferably, 25% by weight of the solid dosage form.

The components of each composition were premixed or blended prior to extrusion. The resulting mixture was blended and then screened through a sieve, for eg, No. 20 (0.85 mm) US standard sieve. The mixture was hot melt extruded to obtain an internal phase. This internal phase was optionally, coated with a coating composition containing a water soluble and alcohol dose-dumping resistance polymer, such as polyvinyl alcohol, hydroxyethyl cellulose, hydroxyethylmethyl cellulose, hydroxypropylmethyl cellulose, sodium alginate, pregelatinized starch, hydroxypropyl starch, alginic acid, sodium carboxymethyl cellulose, sodium starch glycolate, ethyl cellulose and like. The polyvinyl alcohol may be present in the form of various grades such as Opadry® II clear 88 F590007: Polyvinyl alcohol, polyethylene glycol and polysorbate 80, Opadry® II clear 85 F19250: Polyvinyl alcohol, polyethylene glycol and polysorbate 80 and talc and the like. The sodium starch glycolate may be present in various grades but not limited to type A low viscosity, type C high viscosity and the like.

In another embodiment, the internal phase itself contains the drug susceptible to abuse, reverse enteric polymer, part of the antacid such as an alkalizer, water soluble and alcohol dose-dumping resistance polymer. The internal phase so formed is further mixed with part of the antacid and may be converted into a capsule filled with the mixture of internal phase and external phase, or the mixture may be converted into a compressed tablet.

According to one specific aspect, the present invention provides an abuse deterrent immediate release coated reservoir solid dosage form comprising:

a drug susceptible to abuse and a release inhibiting agent, the release inhibiting agent consisting of a combination of at least two polymers and an antacid wherein at least one first polymer is a reverse enteric polymer, and at least one second polymer is alcohol dose-dumping resistance polymer, wherein the reverse enteric polymer and a part of the antacid are present in amounts such that when more than one unit of the dosage form are tested for in-vitro dissolution in 500 ml, of 0.01N HCl, Type II USP apparatus (Paddle) rotating at a speed of 50 rpm, the release is inhibited as compared to the immediate release of drug from a single units in 2 hours when a single unit of the dosage form is tested.

According to another aspect, the present invention provides an abuse deterrent immediate release coated reservoir solid dosage form comprising:

a drug susceptible to abuse and a release inhibiting agent, the release inhibiting agent consisting of a combination of at least two polymers and an antacid wherein at least one first polymer is a reverse enteric polymer, and at least one second polymer is alcohol dose-dumping resistance polymer, wherein the reverse enteric polymer and the antacid are present in amounts such that when more than three units of the dosage form are tested for in-vitro dissolution in 500 ml of 0.01N HCl, Type II USP apparatus (Paddle) rotating at a speed of 50 rpm, the release is inhibited as compared to the immediate release of drug from a single units in 2 hours when a single unit of the dosage form is tested.

The present invention can be said to provide a single method for resolving multiple modes of abuse immediate release solid dosage form comprising a drug susceptible to abuse, the multiple modes of abuse including a. intentional abuse of overdosing or multiple unit administration by an addict or by a subject having suicidal intention, b. intentional abuse of extraction from multiple unit administration by an addict or by a subject having suicidal intention c. unintentional or accidental overdosing, d. concomitant alcohol consumption and resultant drug-alcohol interaction the method comprising:

providing an abuse deterrent immediate release coated reservoir solid dosage form comprising a drug susceptible to abuse and a release inhibiting agent, the release inhibiting agent consisting of a combination of at least two polymers and an antacid wherein at least one first polymer is a reverse enteric polymer, and at least one second polymer is alcohol dose-dumping resistance polymer such that when the prescribed dose in a single unit of the immediate release solid dosage form is administered, the drug is released at a desired rate for quick onset of action, however if more than one unit of the immediate release solid dosage form are administered, the release of the drug is suppressed; or when a single unit of the immediate release dosage form is administered with concomitant alcohol consumption, the drug is released at a reduced rate as compared to the rate of release from a single unit of the immediate release dosage form in a subject who has not consumed alcohol;

when an abuser attempts to extract the drug from multiple units using alcohol or soft drinks, composition provides a barrier to extraction when an abuser attempts to extract the drug from multiple units via nasal or parental route.

The abuse deterrent immediate release coated reservoir solid dosage form according to the present invention provides resistance to tampering by either an oral, nasal or parenteral route. An abuser when attempts to tamper the dosage form by oral route, being an immediate release, abuser may ingest more than the prescribed number of units with the aim of achieving high. The inventors have demonstrated that the dosage form provides resistance to tampering by multiple pill administration. If an abuser intends to tamper the coated reservoir solid dosage form of the present invention by crushing and destroying its configuration or by nasal or parenteral means, it was surprisingly found that the dosage form provided resistance to such abuse by not releasing the drug either in the nasal fluids or in aqueous medium, respectively. Particularly, resistant to such abuse are embodiments where the drug is present as a solid solution or solid dispersion in the intragranular phase containing the reverse enteric polymer. The solid solution or solid dispersion of the drug with the reverse enteric polymer may be achieved by any techniques known in the art such as hot melt extrusion, hot melt granulation, or dissolving or dispersing the drug and the reverse enteric polymer in a suitable solvent and spray drying. In one specific embodiment, a hot melt extrusion process was employed for achieving the solid solution or solid dispersion of drug and the reverse enteric polymer. In one specific embodiment, the method includes steps of: (a) mixing drug, with a reverse enteric polymer at a temperature sufficiently high to soften or melt the polymer and to melt or dissolve the drug in the polymer, thereby forming a dispersion or solution of drug; and (b) allowing the dispersion or solution to cool. The molten mass may be cooled and then sifted to desirable size and mixed with other excipients, and converted into a solid dosage form. It is possible to incorporate a part of the alkalizer in the dispersion or solution formation step, wherein the drug, reverse enteric polymer and the part of the alkalizer are present in the intragranular phase. This phenomenon was observed when the solid dosage form was tested for its tamper resistance in the acidic media such as citric acid, it provided a lesser dissolution indicating that the solid dosage form having alkalizer in the intragranular phase presents a better control over the resistance to tampering. Incorporation of part of the alkalizer in the intragranular phase, also creates difficulty for the abuser to separate the drug, reverse enteric polymer from the alkalizer, as these are agglomerated together to form particles.

In yet another aspect, the present invention provides an abuse deterrent immediate release solid dosage form comprising:

a drug susceptible to abuse and a release inhibiting agent, the release inhibiting agent consisting of a combination of at least two polymers and an antacid wherein at least one first polymer is a reverse enteric polymer, and at least one second polymer is alcohol dose-dumping resistance polymer, wherein the antacid is an $H_2$ antagonist.

The present invention provides a method of achieving deterrence to an abuse, wherein the abuse is effected by ingestion of more than prescribed number of units of the solid dosage form, the abuse being either intentional or unintentional. The solid dosage form according to one of the embodiments of the present invention is tested for pharmacokinetic parameters such as plasma concentration levels by orally administering more than prescribed number of units such as three. It is found that there is a reduction in the maximum plasma concentration ($C_{max}$) when three units of the solid dosage form were administered as compared to the expected $C_{max}$. Expected $C_{max}$ is the plasma level theoretically achieved if three tablets of test product were ingested. This shows that the immediate release biphasic matrix solid dosage form of the present invention provides deterrence to abuse via administration of more than the prescribed number of units. The reduced $C_{max}$ thus provides deterrence to the abuser who attempts to abuse the active ingredient and achieve 'high' by taking more than prescribed number of units of the solid dosage form concurrently.

While the present invention is disclosed generally above, additional aspects are further discussed and illustrated with reference to the examples below. However, the examples are presented merely to illustrate the invention and should not be considered as limitations thereto.

EXAMPLE 1-2

TABLE 1

Immediate release solid dosage form of Example 1 and Example 2

| | | Quantity | | | |
|---|---|---|---|---|---|
| | | mg/Tablet | | % w/w | |
| Description of dosage form | Ingredients | Example 1 | Example 2 | Example 1 | Example 2 |
| Drug reverse enteric polymer granules | TapentadolHCl | 17.40 | 17.40 | 2.45 | 2.43 |
| | Microcrystalline cellulose | 70.10 | 70.10 | 9.89 | 9.80 |
| | Crospovidone | 27.50 | 27.50 | 3.88 | 3.84 |
| | Povidone | 20.00 | 20.00 | 2.82 | 2.79 |
| | Purified water | q.s. | q.s. | | |
| | Methyl methacrylate butyl methacrylate-dimethylaminoethyl methacrylate copolymer (Eudragit® E PO) | 10.40 | 15.66 | 1.46 | 2.18 |
| | Glyceryl monostearate | 0.96 | 1.44 | 0.13 | 0.20 |
| | Talc | 2.10 | 3.14 | 0.29 | 0.43 |
| | Isopropyl alcohol | q.s. | q.s. | | |
| | Purified water | q.s. | q.s. | | |
| | Coated pellets | 148.50 | 155.24 | | |
| Extragranular | Sodium bicarbonate | 560 | 560 | 79.04 | 78.29 |

Tapentadol hydrogen chloride, microcrystaline cellulose and crospovidone were sifted through suitable sieve and mixed. Binder solution was prepared by adding povidone to the vortex of purified water and stirred to form a clear solution. The granulation was done in rapid mixture granulator. The wet granules were extruded through an extruder equipped with suitable screen and spheronized. Pellets were dried and sized and required size fraction of pellets used for coating.

Methyl methacrylate butyl methacrylate-dimethylaminoethyl methacrylate copolymer (Eudragit® E PO) was dissolved in isopropyl alcohol and water. Glyceryl monostearate and talc were added in the solution under stirring using an overhead stirrer. Then the tapentadol HCl pellets were coated in fluid bed processor (FBP) with the solution up to ~10% and ~15% weight gain of example 1 and 2, respectively. Then the coated pellets were mixed with sodium bicarbonate and filled into hard gelatin capsules.

Table 2 provides in vitro dissolution profile (% Release) for N units of the dosage form of the present invention.

| | % drug released | | | |
|---|---|---|---|---|
| | Example 1 | | Example 2 | |
| Time in minutes | N = 1 (A) | N = 3 (B) | N = 1 (A) | N = 3 (B) |
| 0 | 0 | 0 | 0 | 0 |
| 10 | 65 | 9 | 33 | 2 |
| 20 | 96 | 27 | 78 | 7 |
| 30 | 100 | 44 | 94 | 18 |
| 45 | 101 | 64 | 98 | 36 |
| 60 | 101 | 75 | 99 | 51 |

The percent inhibition of release was calculated as follows:

*% inhibition of release with $N$ units $= (A-B/A) \times 100$

Where, A = % release when N=1 and B = % release with N units

TABLE 3

Percent inhibition of release by Examples 1 and Example 2

| | % inhibition of release with N units* | |
|---|---|---|
| Time in minutes | Example 1 N = 3 | Example 2 N = 3 |
| 10 | 86 | 94 |
| 20 | 72 | 91 |
| 30 | 56 | 81 |
| 45 | 37 | 63 |
| 60 | 26 | 48 |

As dosage forms intended for quick onset of action are given a number of times a day as compared to slow release forms that are given at a lower frequency for example once-a-day, they contain a lower amount of drug than in the extended release form. An abuser will want to receive higher amounts by taking multiple units. Therefore, the percent of prescribed dose that an abuser will release at 30 min and 60 min for absorption by taking multiple units of the dosage form was calculated. The prescribed dose is the amount contained in a single unit of the dosage form. Table 1 shows the results for Examples 1 and 2.

TABLE 4

Estimated percent prescribed dose release at 30 minutes and 60 minutes upon abuse by multiple unit administration of the coated reservoir type dosage form of the present invention

| | $D_{30}$* | | $D_{60}$* | |
|---|---|---|---|---|
| Examples | N = 1 | N = 3 | N = 1 | N = 3 |
| 1 | 100 | 132 | 101 | 225 |
| 2 | 94 | 54 | 99 | 153 |

*$D_{30}$ = Percent prescribed dose released in 30 minutes = (Total amount released in 30 mins/amount in prescribed number of units of the dosage form) × 100
*$D_{60}$ = Percent prescribed dose released in 60 minutes = (Total amount released in 60 mins/amount in prescribed number of units of the dosage form) × 100

The results demonstrated that the coated reservoir type system can be formulated such that when a patient takes a single unit he will release the desired single dose of the drug in 30 to 60 minutes for quick onset of action but the abuser will not succeed in achieving a release of more than about 1.5 times the prescribed dose at 30 min by orally administering three units of the dosage form. Preferred Example 2 further demonstrates that the coated reservoir type system can be formulated such that absorption greater than about 1.5 times the prescribed dose is not achieved even at 60 minutes.

EXAMPLE 3-4

TABLE 5 composition details of the dosage form

| | | EXAMPLE 3 | | | EXAMPLE 4 | | |
|---|---|---|---|---|---|---|---|
| | Ingredients | mg per capsule | % by weight of the capsule | % by weight of the Phase | mg per capsules | % by weight of the capsules | % by weight of the Phase |
| Phase I Intragranular | Amitriptyline HCl | 10.0 | 2.227 | 15.15 | 10.00 | 3.584 | 15.15 |
| | Microcrystalline cellulose | 25.0 | 5.567 | 37.87 | 25.00 | 8.960 | 37.87 |
| | Magnesium oxide | 5.00 | 1.113 | 7.575 | 5.00 | 1.792 | 7.575 |
| | Mannitol | 20.0 | 4.45 | 30.2 | 20.0 | 7.17 | 30.2 |
| | Methylmethacrylate and diethylaminoethyl methacrylate copolymer aqueous dispersion | 4.080 | 0.908 | 6.18 | 4.080 | 1.462 | 6.18 |
| | Dibutyl sebacate | 0.500 | 0.111 | 0.76 | 0.500 | 0.179 | 0.76 |
| | Talc | 1.420 | 0.316 | 2.15 | 1.420 | 0.508 | 2.15 |
| Phase II Extragranular | Sodium bicarbonate | 280 | 62.36 | 73.11 | 100 | 35.842 | 46.948 |
| | Magnesium oxide | — | | | 10 | 3.584 | 4.694 |

The core pellets were prepared as follows;

The amitriptyline hydrochloride, microcrystalline cellulose, magnesium oxide and mannitol were sifted. The sifted ingredients were mixed and granulated using aqueous solution of mannitol as a binding agent. The wet granules so formed, were extruded through an extruder. The extrudates were dried and sifted. The dried extrudates were coated with Methylmethacrylate and diethylaminoethyl methacrylate copolymer aqueous dispersion containing talc and dibutyl sebacate. The coating was continued to weight gain of about 10%. The coated extrudates were dried. The coated extrudates along with sodium bicarbonate and magnesium oxide were filled into the capsules.

The filled capsules were subjected to in vitro dissolution in a 500 ml 0.01N HCl in a USP Type II apparatus rotating at a speed of 75 rpm. The deterrence to overdose by multiple pill administration was checked by subjecting more than the prescribed number of units, for example, three capsules, to the in vitro dissolution test. The results of the in vitro dissolution are provided below:

TABLE 6

In vitro dissolution of amitriptyline capsules

| Time in minutes | Example 3 Number of Units tested | | Example 4 Number of Units tested | |
|---|---|---|---|---|
| | n = 1 | n = 3 | n = 1 | n = 3 |
| 5 | 18 | 5 | 22 | 10 |
| 15 | 34 | 10 | 53 | 16 |
| 30 | 58 | 17 | 79 | 21 |
| 60 | 90 | 30 | 100 | 29 |

EXAMPLE 5

TABLE 7 composition details of the dosage form

| | Ingredients | mg/cap | % by wt | % by wt of phase |
|---|---|---|---|---|
| Intragranular phase | Amitriptyline hydrochloride | 10.0 | 2.6 | 12.2 |
| | Microcrystalline cellulose | 25.0 | 6.5 | 30.5 |
| | Magnesium oxide (Light) | 5.0 | 1.3 | 6.10 |
| | Mannitol | 20.0 | 5.2 | 24.4 |
| | Polyvinyl alcohol* | 3.0 | 0.8 | 3.7 |
| | Methyl methacrylate and diethylaminoethyl methacrylate copolymer aqueous dispersion (Kollicoat Smartseal ® 30D) # | 5.9 | 1.53 | 7.2 |
| | Ethyl cellulose aqueous dispersion (Aquacoat ® ECD-30) # | 3.9 | 1.0 | 4.8 |

TABLE 7-continued composition details of the dosage form

|  | Ingredients | mg/cap | % by wt | % by wt of phase |
|---|---|---|---|---|
|  | Dibutyl sebacate | 1.5 | 0.4 | 1.8 |
|  | Talc | 7.6 | 2.0 | 9.3 |
| Extragranular phase | Sodium bicarbonate | 200.0 | 512.0 |  |

*Opadry ® II clear 85F19250 #

Amitriptyline hydrochloride, microcrystalline cellulose, magnesium oxide and mannitol were sifted together and mixed by rapid mixer granulator. The sifted and mixed ingredients were granulated with mannitol solution and extruded through an extruder. The extrudes were spheronised and dried in a fluid bed drier. The dried extrudates were sifted and coated with alcohol dose dumping resistance polymer, polyvinyl alcohol (Opadry® II) to a weight gain of about 5%. Talc, dibutyl sebacate, Kollicoat Smartseal® 30D was mixed with ethyl cellulose dispersion and was coated on the Opadry® coated extrudates to a weight gain of about 30% and further dried in the processor. The dried extrudates and sodium bicarbonate were filled in hard gelatin capsules.

The capsules were tested for dissolution in media namely 0.01N HCl/500 ml/Paddle apparatus at 75 rpm and 0.01N HCl containing 40% alcohol/500 ml/Paddle apparatus at 75 rpm. The results of the dissolution are provided as below:

TABLE 8

In vitro dissolution of amitriptyline capsules in 0.01N HCl

| Time in minutes | Number of Units tested N = 1 | Number of Units tested N = 3 | Number of Units tested N = 10 |
|---|---|---|---|
|  | % dissolved |  |  |
| 5 | 17 | 1 | 0 |
| 15 | 51 | 3 | 1 |
| 30 | 84 | 7 | 2 |
| 60 | 101 | 12 | 4 |

The result in Table 8 indicates that the percentage dissolution is inhibited when more than the prescribed number of units is tested as compared to the dissolution of a prescribed number of units. For example, in case of one unit, release of amitriptyline hydrochloride was complete in 60 minutes, whereas in case of three units, the percentage of release was only 12% (equivalent to 3.6 mg of Amitriptyline hydrochloride which is less than even one unit. When ten units were tested, the release of Amitriptyline hydrochloride was only 4% in 60 minutes which is equivalent to 4 mg of Amitriptyline hydrochloride which is even less than one unit.

TABLE 9

In vitro dissolution of amitriptyline capsules in 0.01N HCl containing 40% v/v alcohol

| Time in minutes | Number of Units tested N = 1 | Number of Units tested N = 3 |
|---|---|---|
|  | % dissolved |  |
| 5 | 0 | 0 |
| 15 | 8 | 3 |
| 30 | 30 | 13 |
| 60 | 68 | 43 |

It is seen from the dissolution data provided in Table 9, that the dissolution was inhibited when more than the prescribed number of units was tested, as compared to the dissolution of a single unit. In case of one unit, release of Amitriptyline hydrochloride was 68% in 60 minutes. In case of three units, the release was 43% in 60 minutes.

EXAMPLE 6

TABLE 10 composition details of the dosage form of Example 6

|  | Ingredients | mg/cap | % by wt of phase | % by wt of cap |
|---|---|---|---|---|
| Intragranular phase | Alprazolam | 1.0 | 1.22 | 0.3 |
|  | Microcrystalline cellulose(Avicel ® PH 101) | 39.0 | 47.6 | 10.1 |
|  | Mannitol | 20.0 | 24.4 | 5.2 |
|  | Polyvinyl alcohol | 3.0 | 3.7 | 0.8 |
|  | Methyl methacrylate and diethylaminoethyl methacrylate copolymer aqueous dispersion (Kollicoat Smartseal ® 30D) | 5.9 | 7.2 | 1.5 |
|  | Ethyl cellulose aqueous dispersion (Aquacoat ® ECD-30) | 3.9 | 4.78 | 1.02 |
|  | Dibutyl sebacate | 1.5 | 1.8 | 0.4 |
|  | Talc | 7.6 | 9.30 | 2.0 |
| Extragranular phase | Sodium bicarbonate | 200.0 | 100.0 | 52.0 |

Alprazolam, microcrystalline cellulose and mannitol were co-sifted together and mixed in a rapid mixer granulator. Mixed ingredients were granulated with purified water. Wet granules were extruded through extruder. Extrudates were spheronized to form round pellets and dried in a fluid bed drier. Dried pellets were sifted through ASTM #20 sieve and pellets retained on ASTM #40 sieve were collected. Opadry® II clear was sifted and added to water under stirring to form a dispersion. Pellets were coated with Opadry® dispersion in fluid bed processor to a weight gain of about 5%.

Talc, Dibutyl sebacate, Kollicoat Smartseal® 30D was mixed with ethyl cellulose dispersion and was coated on the Opadry® coated extrudates to a weight gain of about 30% and further dried in the processor. The dried extrudates and sodium bicarbonate were filled in hard gelatin capsules.

For dissolution of one capsule and three capsules, USP dissolution apparatus type I (basket) was used at 100 rpm speed. For dissolution of ten capsules, USP dissolution apparatus type II (paddle) was used at 75 rpm speed.

TABLE 11

In-vitro dissolution of Alprazolam capsules in 500 ml of 0.01N HCl

| Time in minutes | No. of units tested (N = 1) % Dissolved | No. of units tested (N = 3) % Dissolved | No. of units tested (N = 10) % Dissolved |
| --- | --- | --- | --- |
| 5 | 3 | 0 | 0 |
| 15 | 35 | 2 | 0 |
| 30 | 61 | 16 | 2 |
| 60 | 86 | 42 | 7 |

For dissolution of one capsule and three capsules, USP dissolution apparatus type I (basket) was used at 100 rpm speed. For dissolution of ten capsules, USP dissolution apparatus type II (paddle) was used at 75 rpm speed.

TABLE 12

In-vitro dissolution of Alprazolam capsules in 0.01N HCl containing 40% alcohol/500 ml

| Time in minutes | No. of units tested (N = 1) % Dissolved | No. of units tested (N = 3) % Dissolved | No. of units tested (N = 10) % Dissolved |
| --- | --- | --- | --- |
| 5 | 0 | 0 | 0 |
| 15 | 3 | 1 | 1 |
| 30 | 15 | 4 | 4 |
| 60 | 21 | 10 | 9 |

EXAMPLE 7

The intragranular phase was prepared by mixing drug and the reverse enteric polymer and subjecting the mixture to hot melt extrusion. The extrudates were milled and were subjected to X-ray diffraction along with physical mixture of the drug and the reverse enteric polymer, drug alone and the blend of Methyl methacrylate and Diethyl aminoethyl methacrylate copolymer in the powder form and polyvinyl alcohol but without drug (referred to as placebo).

TABLE NO. 13

Composition details of the intragranular phase

| Sr.No. | Ingredients | Quantity in mg | % by wt |
| --- | --- | --- | --- |
| 1 | Tapentadol HCl | 11.6 | 10.78 |
| 2 | Methyl methacrylate and Diethyl aminoethyl methacrylate copolymer* powder form | 80.0 | 74.4 |
| 3 | Polyvinyl alcohol** | 16..0 | 14.9 |

Opadry II clear 88F590007 contains Polyvinyl alcohol** 75.66%, PEG 21.34% and Polysorbat 80--3.0%.

Procedure: The specified amounts of tapentadol, Methyl methacrylate and Diethyl aminoethyl methacrylate copolymer in the powder form and polyvinyl alcohol were mixed. The blend was subjected to hot melt extrusion at a temperature of about 155° –160° C. The extrudates so prepared were milled and sifted through suitable sieve. The milled extrudes were subjected to XRD diffraction. The XRD is given in FIG. 20.

What is claimed is:

1. An abuse deterrent immediate release coated reservoir solid dosage form comprising:
   A) an intragranular phase comprising
      i) core containing drug susceptible to abuse and a first part of an alkalizer,
      ii) a coating comprising a reverse enteric polymer, said coating surrounding the core to form a coated reservoir, said coating not containing an alkalizer; and
   B) an extragranular phase comprising a second part of the alkalizer,
   wherein the coated reservoir and the extragranular phase are mixed and filled into capsules,
   wherein the drug susceptible to abuse is selected from the group consisting of an opioid, a central nervous system depressant and a central nervous system stimulant, and
   wherein the reverse enteric polymer is a copolymer comprising methylmethacrylate and diethylaminoethyl methacrylate that is soluble at an acidic pH but is insoluble at a second acidic pH of 5.5,
   wherein when a single unit or a prescribed number of units of the immediate release solid dosage form is administered, the drug is released at a desired rate, but when more than the prescribed number of units of the immediate release solid dosage form are administered, the amount of alkalizer contained in the solid dosage forms is sufficient to raise the stomach pH to above the solubility point of the reverse enteric polymer, whereby the release of the drug is suppressed, and
   wherein the dosage form is in the form of a capsule.

2. The abuse deterrent immediate release coated reservoir solid dosage form according to claim 1,
   wherein the drug susceptible to abuse is present in the intragranular phase as a solid dispersion.

3. The abuse deterrent immediate release coated reservoir solid dosage form according to claim 1,
   wherein the solid dosage form further comprises an alcohol dose dumping resistance polymer.

* * * * *